US006506168B1

(12) United States Patent
Fathallah et al.

(10) Patent No.: US 6,506,168 B1
(45) Date of Patent: Jan. 14, 2003

(54) APPARATUS AND METHOD FOR OBTAINING BLOOD FOR DIAGNOSTIC TESTS

(75) Inventors: Marwan A. Fathallah, Mundelein, IL (US); Geoffrey R. Chambers, Middlesex (GB)

(73) Assignee: Abbott Laboratories, Abbott Park, IL (US)

(*) Notice: Subject to any disclaimer, the term of this patent is extended or adjusted under 35 U.S.C. 154(b) by 0 days.

(21) Appl. No.: 09/579,906

(22) Filed: May 26, 2000

(51) Int. Cl.[7] .................................................. B61B 5/00
(52) U.S. Cl. ...................................... 600/578; 606/181
(58) Field of Search ............................... 600/573, 574, 600/575, 576, 577, 578, 579, 580, 581–84; 606/180, 181, 182

(56) References Cited

U.S. PATENT DOCUMENTS

| | | |
|---|---|---|
| 4,203,446 A | 5/1980 | Hofert et al. |
| 4,653,513 A | 3/1987 | Dombrowski |
| 4,775,361 A | 10/1988 | Jacques et al. |
| RE32,922 E | 5/1989 | Levin et al. |
| 4,990,154 A | 2/1991 | Brown et al. |
| 5,035,704 A | 7/1991 | Lambert et al. |
| 5,165,418 A | 11/1992 | Tankovich |
| 5,320,607 A | 6/1994 | Ishibashi |
| 5,374,556 A | 12/1994 | Bennett et al. |
| 5,487,748 A | 1/1996 | Marshall et al. |
| 6,027,459 A | 2/2000 | Shain et al. |

FOREIGN PATENT DOCUMENTS

| | | |
|---|---|---|
| EP | 0 449525 A1 | 2/1991 |
| WO | 94/09713 | 11/1994 |
| WO | 98/24366 | 11/1998 |

OTHER PUBLICATIONS

Lane, et al., "Ultraviolet–Laser Ablation of Skin", *IBM Research Report*, 1984.
U.S. application Ser. No. 08/759,698, filed Dec. 6, 1996.
U.S. application Ser. No. 08/982,323, filed Dec. 2, 1997.
U.S. application Ser. No. 08/982,324, filed Dec. 2, 1997.
U.S. application Ser. No. 08/982,721, filed Dec. 2, 1997.

*Primary Examiner*—Kevin Shaver
*Assistant Examiner*—Pamela L. Wingood
(74) *Attorney, Agent, or Firm*—David L. Weinstein

(57) ABSTRACT

Method and apparatus for obtaining a sample of blood from a patient for subsequent diagnostic tests, e.g., glucose monitoring. In one aspect of the invention, an apparatus for carrying out the method described previously is provided. The apparatus comprises:

(a) a housing having a sealable chamber located therein and a sealable opening in fluid communication with the sealable chamber;

(b) a vacuum pump in communication with the sealable chamber;

(c) a device for forming an unobstructed opening in an area of skin from which a sample is to be collected, preferably a lancing assembly, the device positioned within the sealable chamber;

(d) a movable support for supporting and positioning a port for a fluid collector in the sealable chamber, the movable support capable of moving the port within the sealable chamber between a first position and a second position; and (e) a stop for aligning the fluid collector.

In another aspect of the invention, the method comprises a method for utilizing the aforementioned apparatus.

31 Claims, 12 Drawing Sheets

APPARATUS AND METHOD FOR OBTAINING BLOOD FOR DIAGNOSTIC TESTS

CROSS REFERENCES TO COPENDING APPLICATIONS

This application relates to four patent applications, each entitled METHOD AND APPARATUS FOR OBTAINING BLOOD FOR DIAGNOSTIC TESTS, U.S. Ser. No. 08/759,698 now U.S. Pat. No. 6,063,039, filed Dec. 6, 1996, U.S. Ser. No. 08/982,323, now U.S. Pat. No. 6,071,251 filed Dec. 2, 1997, U.S. Ser. No. 08/982,324, now U.S. Pat. No. 6,071,249 filed Dec. 2, 1997, and U.S. Ser. No. 08/982,721, now U.S. Pat. No. 6,093,156 filed Dec. 2, 1997. The specifications, drawings and claims of these applications are in corporated herein by reference. All of the foregoing applications are commonly owned by the assignee of this invention.

BACKGROUND OF THE INVENTION

1. Field of the Invention

This invention relates to a method and apparatus for obtaining samples of blood for diagnostic purposes.

2. Discussion of the Art

The prevalence of diabetes has been increasing markedly in the world. At this time, diagnosed diabetics represent about 3% of the population of the United States. It is believed that the total actual number of diabetics in the United States is over 16,000,000. Diabetes can lead to numerous complications, such as, for example, retinopathy, nephropathy, and neuropathy.

The most important factor for reducing diabetes-associated complication s is the maintenance of an appropriate level of glucose in the blood stream. The maintenance of the appropriate level of glucose in the blood stream may prevent and even reverse many of the effects of diabetes.

Glucose monitoring devices of the prior art have operated on the principle of taking blood from an individual by a variety of methods, such as by needle or lancet. An individual then coats a paper strip carrying chemistry with the blood, and finally inserts the blood-coated strip into a blood glucose meter for measurement of glucose concentration by determination of change in reflectance.

The medical apparatus of the prior art for monitoring the level of glucose in the blood stream required that an individual have separately available a needle or lancet for collecting blood from the individual, strips carrying blood chemistry for creating a chemical reaction with respect to the glucose in the blood stream and changing color, and a blood glucose meter for reading the change in color indicating the level of glucose in the blood stream. The level of blood glucose, when measured by a glucose meter, is read from a strip carrying the blood chemistry through the well-known process of reading reflectometers for glucose oxidation.

Generally lancets comprise a blade and a pressable end opposed thereto, with the blade having an acute end capable of being thrust into skin of a human. By striking the pressable portion, the acute end of the blade will pierce the skin, for example, of the finger. The finger lancet is primarily used to obtain small volumes of blood, i.e., less than 1 mL. Diabetics use the finger lancet to obtain volumes of blood less than 25 $\mu$L for analysis for glucose. A small amount of blood for the blood test will ooze out of the skin. There are many small blood vessels in each finger so that a finger can be squeezed to cause a larger drop of blood to ooze. The finger is one of the most sensitive parts of the body; accordingly, the finger lancet leads to even more pain than what would be experienced by collecting blood via lancet at a different body site. The finger lancet presents another problem because of the limited area available on the fingers for lancing. Because it is recommended that diabetics monitor their blood glucose levels four to six times per day, the limited area on the fingers calls for repeated lancing of areas that are already sore. Because fingers are sensitive to pain, it is a recent tendency that the arm is subjected to blood sampling. See, for example, U.S. Pat. No. 4,653,513. The device of U.S. Pat. No. 4,653,513 comprises a cylindrical housing and a lancet support, which has a gasket or flexible portion slidably accommodated in the housing. Springs will retract the lancet support to thereby reduce air pressure in the housing so that it sucks a blood sample, automatically and immediately after a lancet pierces the skin. See also U.S. Pat. No. 5,320,607, which discloses a device comprising a sealed vacuum chamber in a state of preexisting reduced pressure, a support member for the sealed vacuum chamber, the support member defining a suction portion adjacent the sealed vacuum chamber, the suction portion, in cooperation with the sealed vacuum chamber, exposing an area of the skin of a patient to a reduced pressure state when the device is actuated, and means arranged within the suction portion for slightly rupturing a portion of the area of skin of the patient exposed to the reduced pressure state.

Because the blood volume requirements for a standard glucose test strip are typically 3 $\mu$L or more, an area of the body that can generate that much blood from a lancet wound must be used. It is believed, however, that improvements in glucose test strip technology will reduce the volume of blood needed to 1 to 3 $\mu$L. Because the finger is well supplied with blood and the amount of blood can be increased by squeezing the finger after lancing, the finger is the currently preferred body site for lancing, even though lancing of the finger is painful.

A less painful technique for obtaining body fluids is described in U.S. Ser. No. 08/982,721, filed Dec. 2, 1997. This application discloses an apparatus for obtaining blood for diagnostic tests. The apparatus comprises a housing having a sealable chamber located therein and a sealable opening in fluid communication with the sealable chamber, a power source, a vacuum pump operably connected to the power source, the vacuum pump in communication with the sealable chamber, a lancing assembly positioned within the sealable chamber, and a fluid collector positioned in the sealable chamber, the fluid collector in fluid communication with the sealable opening. It would be desirable to improve that apparatus in order to ensure that the fluid collector is properly positioned in the apparatus during the lancing and fluid collecting steps.

SUMMARY OF THE INVENTION

This invention provides a method and apparatus for collecting a sample of blood from a patient for subsequent diagnostic tests, e.g., glucose monitoring.

In one aspect of the invention, an apparatus for collecting a sample of body fluid, e. g., blood, for analysis in a diagnostic test is provided. In a preferred embodiment, the apparatus comprises:
  (a) a housing having a sealable chamber located therein and a sealable opening in fluid communication with the sealable chamber;
  (b) a vacuum pump in communication with the sealable chamber;

(c) a device for forming an unobstructed opening in an area of skin from which a sample is to be collected, preferably a lancing assembly, the device positioned within the sealable chamber;

(d) a movable support for supporting and positioning a port for a fluid collector in the sealable chamber, the movable support capable of moving the port within the sealable chamber between a first position and a second position; and (e) a stop for aligning the fluid collector.

In more preferred embodiments, the apparatus further comprises a power source, and the vacuum pump is operably connected to the power source. The stop aligns the fluid collector so that the fluid collector is capable of being properly positioned in the apparatus during the lancing and fluid collecting steps.

The fluid collector is preferably a test strip that contains at least one chemical reagent for conducting a diagnostic test, e.g., a test for determining blood glucose level. Typically the test strip has an opening formed therein, which opening is capable of being aligned with the sealable opening of the housing. A preferred device for forming an unobstructed opening in the area of the skin from which the sample of blood is to be collected is a lancing assembly, which comprises a lancet for forming an opening in the skin. Alternatively, the unobstructed opening in the skin can be formed by a laser or by a fluid jet. In the case of a lancing assembly, when the lancing assembly is triggered, the lancet of the lancing assembly passes through the opening of the test strip and the sealable opening of the housing to form an opening in the skin of the patient. The sample of body fluid, e.g., blood, is obtained from the opening formed in the skin of the patient. The opening of the test strip should be properly aligned with the sealable opening of the housing before the lancing assembly is triggered, because misalignment of these openings may result in one or more of the following undesirable occurrences: (1) an unsuccessful assay; (2) a longer period of time required to collect an adequate amount of sample; (3) extensive contamination of the apparatus by the sample. The movable support (d) and the stop (e) are designed to operate in concert to ensure that the opening of the test strip and the sealable opening of the housing are properly aligned. By designing the movable support to move the fluid collector port from a first position to a second position, the opening in the test strip can be properly aligned with the sealable opening in the housing, thereby ensuring that the assay can be conducted successfully.

The vacuum pump requires a power source. The power source can be disposed within the housing. Alternatively, the power source can be external to the housing. The vacuum pump can serve the dual purposes of (1) stretching the skin and (2) enhancing the collection of the sample of blood from the unobstructed opening in the skin. Preferably, the vacuum pump can serve the triple purposes of (1) stretching the skin, (2) increasing the availability of blood to the area of the skin from which the sample is to be collected, and (3) enhancing the collection of the sample of blood from the unobstructed opening in the skin.

The housing comprises a body and a cover. The sealable chamber is located within the cover. The cover is separated from the body so that the test strip can be inserted into a test strip port located in the volume that is to be enclosed by the cover when the cover is closed against the body of the housing. After the test strip is inserted in the test port, the cover is closed against the body to form a chamber that will be sealed when the sealable opening of the housing is placed in contact with the skin of a patient. Preferably, the body of the housing contains electronics having programmed instructions to control the vacuum pump to maintain the desired level of vacuum for the method of this invention.

The apparatus preferably contains valves, such as, for example, solenoid valves, for triggering the lancet of the lancing assembly and releasing the vacuum at the conclusion of the blood collection procedure. The apparatus can optionally contain a heating element to increase the availability of blood to the area of the skin from which the sample is to be collected.

In another aspect of the invention, a method for collecting a sample of body fluid, e.g., blood, for analysis in a diagnostic test is provided. In general, the method comprises the steps of:

(a) inserting a fluid collector into the port;

(b) aligning the fluid collector latitudinally and longitudinally so that an opening in the fluid collector is aligned with the sealable opening of the housing of the apparatus;

(c) placing the sealable opening of the housing against the skin of the patient;

(d) forming an unobstructed opening in the area of the skin from which the sample of blood is to be collected;

(e) aligning the fluid collector longitudinally so that an opening in the fluid collector is aligned with the sealable opening of the housing of the apparatus; and (f) collecting the sample of blood from the unobstructed opening in the skin onto the fluid collector, with the aid of vacuum and stretching of the skin.

In order to insert a fluid collector into the support, the cover is separated from the body of the housing; then the fluid collector, e.g., a test strip, is inserted into the port for the fluid collector; and then the cover is closed against the body of the housing. The movable support is actuated to cause the port to move from a first position to a second position in order to align an opening in the fluid collector with the sealable opening of the housing of the apparatus.

In a preferred embodiment of the method, step (d) is preceded by the step of increasing the availability of blood in the portion of the skin from which the sample is to be collected. In this preferred embodiment, the availability of blood in the portion of the skin from which the sample is to be collected can be increased by means of a vacuum, which is applied to the surface of the skin in the vicinity of the opening prior to forming the opening in the skin. The vacuum causes the portion of the skin in the vicinity of the blood collection site to become engorged with blood. The vacuum also causes the portion of the skin in the vicinity of the blood collection site to become stretched.

An opening in this stretched portion of skin can be formed with a cutting or puncturing device, e.g., a lancet, or other device capable of forming an opening in the skin, e.g., a laser or a fluid jet. If a cutting or puncturing device is used to form the opening, it must be retracted from the opening prior to the step of collecting the sample of blood from the opening. This retraction will allow the unrestricted flow of blood through the opening. After the opening is formed, the movable support is moved from the first position to the second position in order to align the opening in the fluid collector with the sealable opening of the housing of the apparatus. Then a vacuum can be used to aid in collecting the sample of blood from the opening in the skin.

The method and apparatus of this invention provide several advantages over the methods and apparatus of the prior art. First, a sufficient amount of blood can be collected from parts of the body, other than the finger, for conducting glucose monitoring tests. Second, by rendering other parts of the body suitable for collecting blood, the use of a painful finger lance can be avoided. Third, by increasing the availability of blood at the site where the blood is to be collected, the period of time required for collecting the sample can be reduced. Fourth, by improving the registration of the opening in the fluid collector (e.g., test strip) with the sealable opening in the housing, both the likelihood that the lancet will strike a solid portion of the fluid collector during the lancing step and the likelihood that an insufficient amount of sample will be collected will be reduced. Because of these advantages, the diabetic patient is more likely to monitor glucose levels in the blood at the intervals prescribed by his doctor.

BRIEF DESCRIPTION OF THE DRAWINGS

In FIGS. 1A and 1B, the cover of the housing of the apparatus is closed against the body of the housing of the apparatus.

In FIG. 3C, the cover is in its closed position.

FIG. 5A shows the switch in the OPEN position, i.e., the assay is not yet ready to be run. FIG. 5B shows the switch in the CLOSED position, but the fluid collector is not in proper register. FIG. 5C shows the switch in the CLOSED position, and the fluid collector is in proper register.

FIG. 7A shows the fluid collector and the alignment mechanism assembly prior to the registration procedure. FIG. 7B shows the fluid collector and the alignment mechanism assembly during the registration procedure. FIG. 7C shows the fluid collector and the alignment mechanism assembly after the registration procedure and prior to the lancing procedure. The components of the alignment mechanism assembly in FIGS. 7B and 7C are identical to those of the alignment mechanism assembly in FIG. 7A. Therefore, reference numerals that are not relevant to the registration procedure are not restated in FIGS. 7B and 7C.

FIG. 8A shows the lancing assembly prior to the triggering thereof. FIG. 8B shows the lancing assembly during the lancing procedure. FIG. 8C shows the lancing assembly after the lancet has been retracted from skin of the test subject. The components of the alignment mechanism assembly in FIGS. 8B and 8C are identical to those of the alignment mechanism assembly in FIG. 8A. Therefore, reference numerals that are not relevant to the lancing procedure are not restated in FIGS. 8B and 8C.

FIG. 9A shows the sample collection procedure prior to the movement of the alignment mechanism assembly but subsequent to the formation of the opening in the skin of the test subject. FIG. 9B shows the sample collection procedure subsequent to the movement of the alignment mechanism assembly toward the sample.

DETAILED DESCRIPTION

Figure 1A:
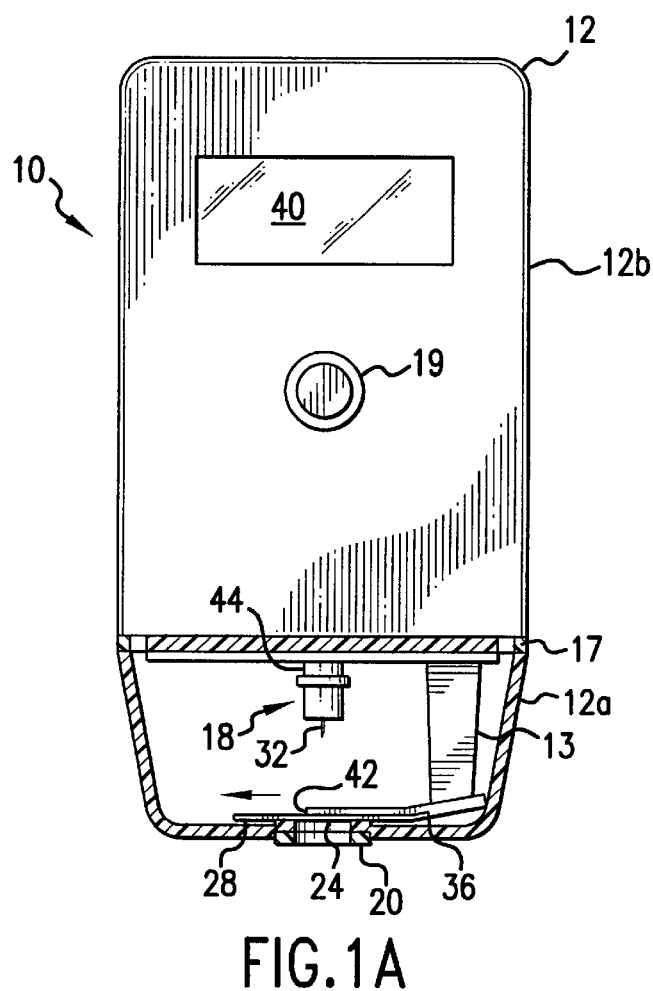
FIGS. 1A and 1B depict partial cross-sectional views of an embodiment of the apparatus of this invention.

As used herein, the terms "register", "registration", and the like refer to a process resulting in correct alignment or positioning. The term "latitudinal" refers to the direction running perpendicular to the flow of fluid in the fluid collector (e.g., test strip). The term "longitudinal" refers to the direction running parallel to the flow of fluid in the fluid collector (e.g., test strip). The term "sample" means a specimen of body fluid. In this invention, the body fluid described is blood. However, it is within the scope of this invention to obtain samples of other types of specimens of body fluid.

The preferred embodiments of the apparatus of this invention utilize the following components to improve the function of obtaining a sample of blood for carrying out a diagnostic test, e.g., determining blood glucose level:

(a) a housing having a sealable chamber located therein and a sealable opening in fluid communication with the sealable chamber;

(b) a vacuum pump in communication with the sealable chamber;

(c) a device for forming an unobstructed opening in an area of skin from which a sample is to be collected, preferably a lancing assembly, the device positioned within the sealable chamber;

(d) a movable support for supporting and positioning a port for a fluid collector in the sealable chamber, the movable support capable of moving the port within the sealable chamber between a first position and a second position; and (e) a stop for aligning the fluid collector.

The components of the apparatus other than the movable support (d) and the stop (e) are described in detail in U.S. Ser. No. 08/759,698, filed Dec. 6, 1996, U.S. Ser. No. 08/982,323, filed Dec. 2, 1997, U.S. Ser. No. 08/982,324, filed Dec. 2, 1997, and U.S. Ser. No. 08/982,721, filed Dec. 2, 1997, and U.S. Pat. No. 6,027,459, all of which are incorporated herein by reference. When relevant, portions of the foregoing applications and patent will be described in detail herein in order to more clearly describe the components involved in the alignment of the opening of the fluid collector with the sealable opening in the housing.

The apparatus of this invention is designed to perform an assay, such as, for example, an assay to determine blood glucose level, by means of a simple procedure involving a minimum of manipulation. The apparatus forms an opening in the skin of the patient, collects the sample, such as, for example, a sample of blood, and measures and reports the desired information relating to the sample. All of the foregoing steps are performed by means of a single apparatus, with all the procedural steps taking place within the apparatus.

The accuracy and reliability of the apparatus and the method require that the fluid collector, hereinafter alternatively referred to as a "test strip", be precisely and correctly aligned within the apparatus. Misalignment of the test strip within the apparatus can possibly result in an unsuccessful formation of an opening in the skin of the patient because of the lancet's hitting the test strip. Moreover, misalignment of the test strip within the apparatus can result in poor sample collection because the sample collection area of the test strip is not aligned with the site of the opening in the skin of the patient. Either type of misalignment can result in an unsuccessful assay (i. e., no results or erroneous results), a longer period of time required to collect an adequate amount of sample, or extensive contamination of the apparatus by the sample. It is possible to ensure precise and correct alignment of the test strip within the apparatus so long as the following procedures are carried out:

(1) manufacture the test strip to proper dimensional specifications;

(2) properly align the properly manufactured test strip in a latitudinal direction; and (3) properly align the properly manufactured test strip in a longitudinal direction.

This invention is concerned with proper alignment of a properly manufactured test strip both in a latitudinal direction and in a longitudinal direction.

The dimensional tolerances with respect to the length and width of a test strip, and the position and diameter of the opening in the test strip, as well as the sample collection area, are closely controlled during the fabrication process in which the test strips are manufactured. The test strips are designed to work in concert with the alignment mechanism assembly to provide an accurate and reliable assay.

Figure 1B:
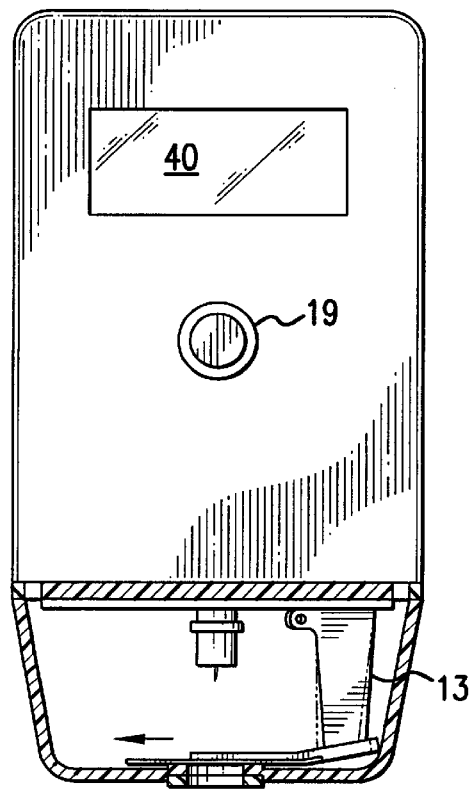
Figure 2A:
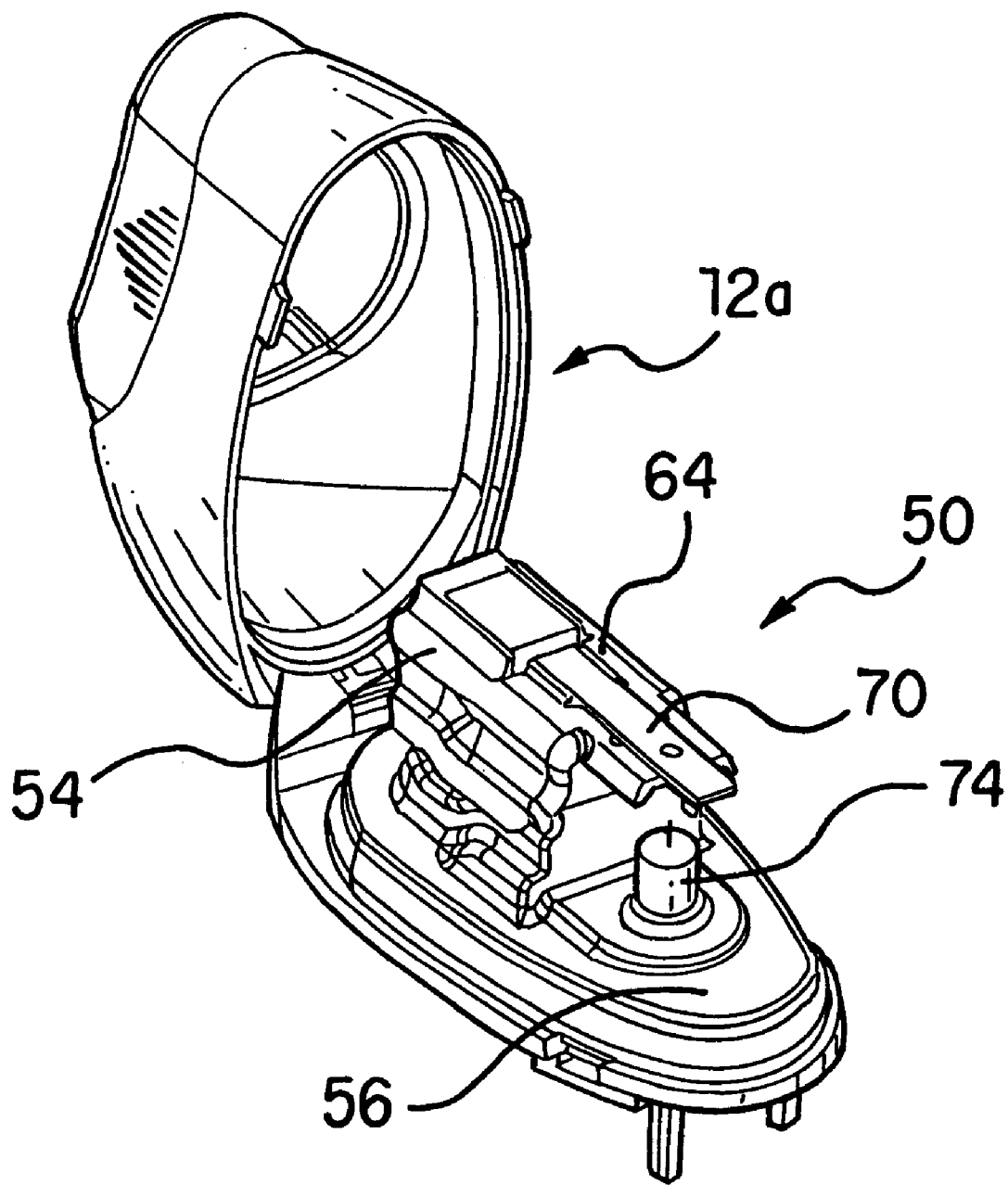
FIG. 2A is a perspective view of the alignment mechanism assembly of this invention. In this figure, the cover is in its open position.
Figure 2B:
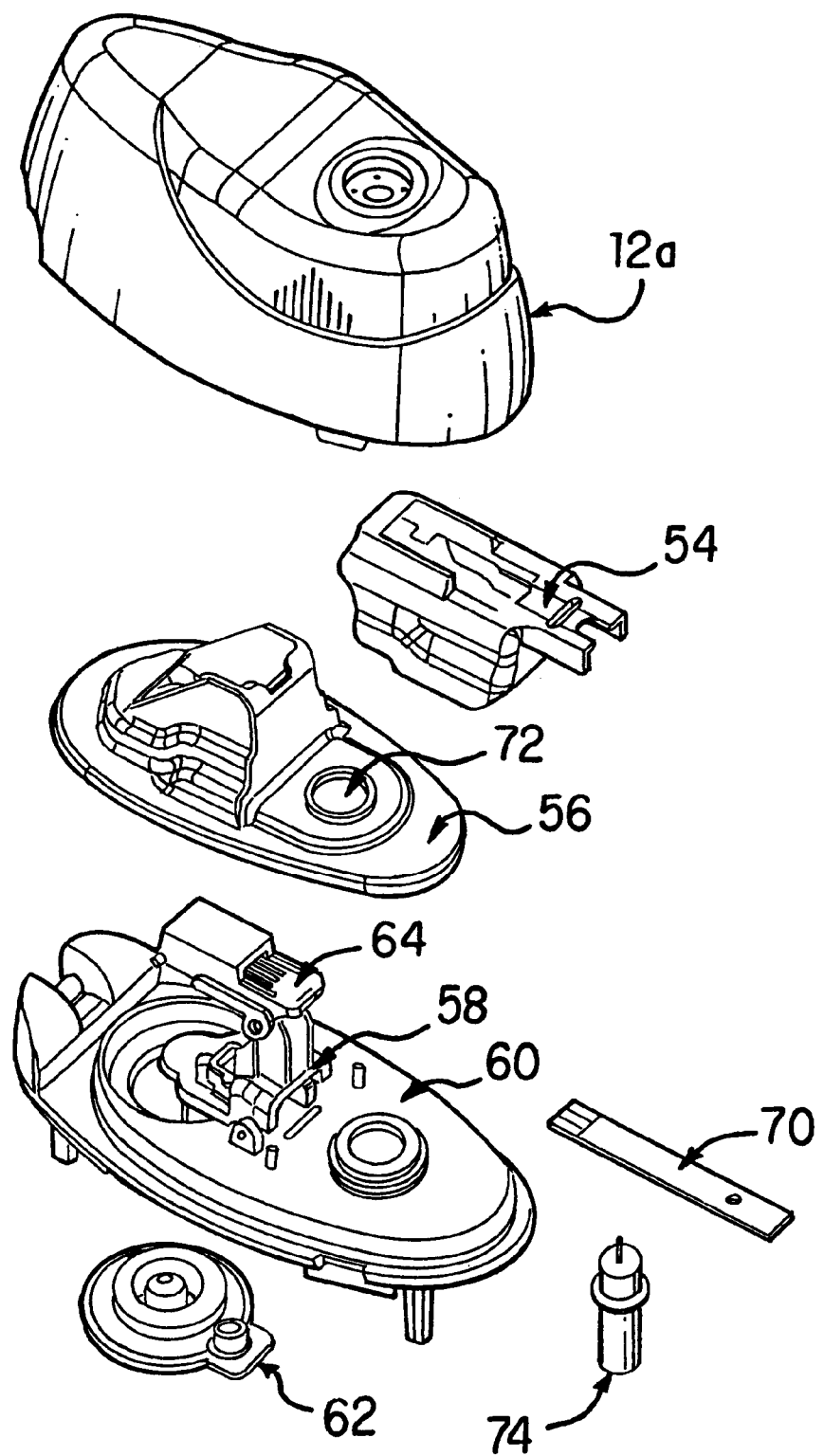
FIG. 2B is an exploded perspective view showing the components of the alignment mechanism assembly of this invention.
Figure 3A:
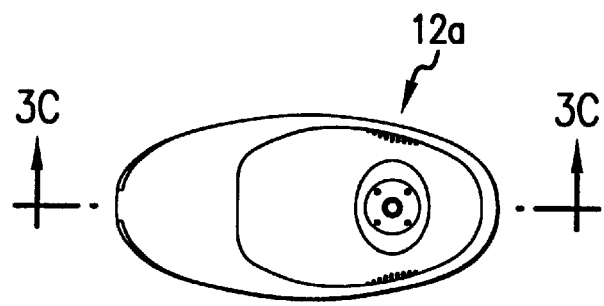
FIG. 3A is a top view of the cover of the housing of the apparatus of this invention.
Figure 3B:
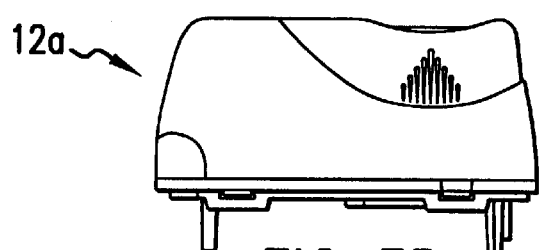
FIG. 3B is a side elevation view of the cover of the housing of this invention.
Figure 3C:
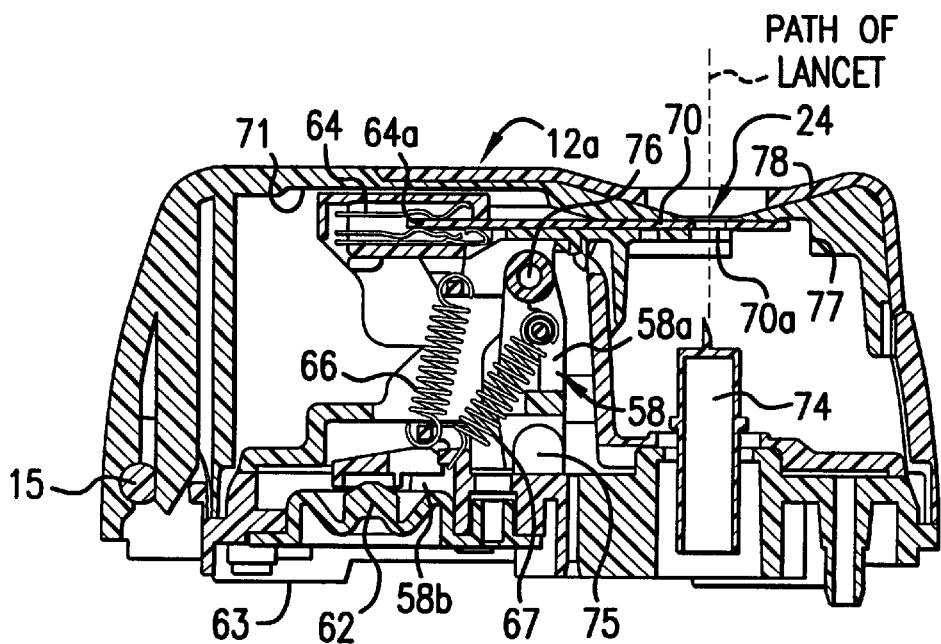
FIG. 3C is a side elevation view, in cross section, taken along line C—C of FIG. 3A, of the alignment mechanism assembly of this invention.

Referring now to FIGS. 1A and 1B, which schematically depict one embodiment of the present invention, the apparatus 10 comprises a housing 12 having a cover 12a (shown in the closed position in FIGS. 1A and 1B). The cover 12a is attached to the body 12b of the housing 12 by an attachment in the form of a hinge (not shown in FIGS. 1A and 1B but shown in FIGS. 3, 7A, 8A, and 9A as reference numeral 15). Alternatively, the cover 12a may be attached to the body 12b by frictional engagement, a detent (not shown), or any combination of a hinge, frictional engagement, and a detent. When a hinge is used, it may optionally be spring biased to retain the cover 12a in the open or closed position. A detent (not shown) may be provided on the cover 12a to engage with a protrusion (not shown) on the body 12b, or vice versa, to maintain the cover 12a in the open or closed position when desired. Although a hinge (not shown in FIGS. 1A and 1B) is utilized in the embodiment shown in FIGS. 1A and 1B, any other attachment or combination of attachments that allows the cover 12a to attach to the body 12b and alternate between an open and closed position is acceptable. A gasket or other seal arrangement 17 is provided to seal the housing 12 when the cover 12a is closed. Additionally, a latch mechanism may be included to prevent accidental opening of the cover 12a when the apparatus 10 is in use. Typically, the latch mechanism would provide locking engagement of the cover 12a with the body 12b.

Disposed within the housing 12 are a vacuum pump (not shown), a lancet assembly 18 generally comprising a molded plastic piece 44 to which a lancet 32 is affixed, a lancing assembly (not shown) into which the lancet assembly 18 is inserted, a battery (not shown), and electronics (not shown) for purposes described hereinafter. A switch 19 is provided to activate the electronics, which may take the form as shown in FIG. 3 of U.S. Ser. No. 08/982,721, filed Dec. 2, 1997, incorporated herein by reference. The vacuum pump communicates by an evacuation tube (not shown) with the volume enclosed by the cover 12a when the cover 12a is in the closed position. Optionally a check valve (not shown) may be placed in the evacuation tube between the vacuum pump and the volume enclosed by the cover 12a when the cover 12a is in the closed position.

During the process of obtaining the sample, the cover 12a is closed to form a seal. The seal should be sufficiently tight so that a sufficient vacuum can be obtained by removing air from the volume enclosed by the cover 12a when the cover 12a is in the closed position.

The area of the cover 12a of the housing 12 that is to contact the skin is equipped with a seal 20. The seal 20 surrounds a sealable opening 24 in the cover 12a as disclosed in U.S. Ser. No. 08/982,721, filed Dec. 2, 1997, incorporated herein by reference. The sealable opening 24 may be round, oval, rectangular or any other shape. The sealable opening 24 in the cover 12a allows communication between the surface of the skin and a blood collection chamber adjacent to a fluid collector, shown here in the form of a glucose detector 28, which may take the shape and form of a test strip. Preferably, the glucose detector 28 contains at least one opening (not shown in FIGS. 1A and 1B) approximately equidistant from the elongated edges of the middle of glucose detector 28 for the lancet 32 to pass through, as disclosed in U.S. Ser. No. 08/982,721, filed Dec. 2, 1997, incorporated herein by reference. In this embodiment, the aforementioned at least one opening in the glucose detector 28 is preferably in alignment with sealable opening 24 and lancet 32 during the lancing step. The opening in the glucose detector 28 may be covered with a mesh. Alternatively, the glucose detector 28 used in the embodiment shown in FIGS. 1A and 1B may contain a semi-circular notch (not shown) in the region of the glucose detector 28 that comes into contact with the blood, as disclosed in U.S. Ser. No. 08/982,323, filed Dec. 2, 1997, incorporated herein by reference. The semi-circular notch may be covered with a mesh. Fluid collectors, such as, for example, glucose detectors, suitable for use in this invention include, but are not limited to, biosensors and reflectance strips. If a biosensor is used, it is preferred that the apparatus 10 include a meter to measure electrical properties, e.g., current, arising from the interaction of a sample with the reagents of the biosensor. If a reflectance strip is used, it is preferred that the apparatus 10 include a meter, e.g., reflectometer, to measure optical properties, e.g., reflectance, arising from the interaction of a sample with the reagents of the reflectance strip.

When in use, the apparatus 10 is positioned so that the lancing assembly is placed over the region on the surface of the skin from which the fluid sample is to be obtained such that the lancing assembly is approximately perpendicular to the surface of the skin. Prior to actuating the apparatus 10, a fluid collector, e.g., a glucose detector in the form of a test strip, is inserted into a slot 36 of a movable projection 13 of the body 12b of the housing 12. The glucose detector 28 contains one or more electrical contacts (not shown) on the end inserted into the slot 36, which contacts engage one or more electrical contacts (not shown) positioned within the slot 36. In order to obtain the sample of blood, the cover 12a of the housing 12 is placed against the skin, whereby the seal 20 surrounding the sealable opening 24 allows a satisfactory vacuum to be effected. The switch 19 is actuated, typically by being pressed, thereby activating the electronics, described in FIG. 3 of U.S. Ser. No. 08/982,721, filed Dec. 2, 1997 and discussed above, which starts the vacuum pump. The action of the vacuum pump withdraws air from the volume enclosed by the cover 12a when the cover 12a is in the closed position and causes the skin circumscribed by the seal 20 to be drawn toward the sealable opening 24. This results in the skin becoming engorged with blood. Engorgement of the skin with blood is accompanied by a stretching of and rising up of the skin to the sealable opening 24 in the cover 12a.

After an appropriate period of time, which is typically pre-set by the programmed electronics, the lancing assembly is triggered, thereby causing the lancet 32 to penetrate the skin that has been pulled up into the sealable opening 24 of the cover 12a. The lancet 32 is preferably triggered automatically by activation of a solenoid valve (not shown) that causes a vacuum-actuated piston (not shown) to trigger the lancet 32, as disclosed in U.S. Pat. No. 6,027,459, incorporated herein by reference.

The description to this point has dealt with apparatus and methods described previously in U.S. Ser. No. 08/982,721, filed Dec. 2, 1997 and shown in FIGS. 1A and 1B. The apparatus particular to this invention will now be described in greater detail. Referring now to FIGS. 2A, 2B, 3A, 3B, 3C, 5A, 5B, 5C, 5D, 6A, 6B, 6C, and 6D, the alignment mechanism assembly 50 comprises the cover 12a, a port shroud 54, a skirt 56, a movable support 58, a vacuum plate 60, a diaphragm 62, a diaphragm plate 63, and a test strip port 64. The movable support 58 is analogous to the movable projection 13 shown in FIGS. 1A and 1B. The test strip port 64, into which a test strip 70 for an assay is inserted, is inserted into an opening 65 in the port shroud 54. The port shroud 54 has a slot 54a formed therein to accommodate any excess fluid from the sample, so that excess fluid does not flow past the slot 54a and consequently contaminate the critical parts of the test strip port 64. The test strip 70 is analogous to the glucose detector 28 shown in FIGS. 1A and 1B. The skirt 56 functions as a means for positioning the vacuum plate 60, the movable support 58, and the diaphragm 62 and as a means for providing a base for the movable support 58 and the vacuum plate 60. A first resilient biasing element 66, e.g., a spring, connects the test strip port 64 to the vacuum plate 60. A second resilient biasing element 67, e.g., a spring, connects the movable support 58 to the vacuum plate 60. The first resilient biasing element 66 operates to bias one end 54b of the port shroud 54 upwards, so that the user of the apparatus can easily insert a test strip 70 into the test strip port 64, which is carried in the port shroud 54. The upper surface of the port shroud 54 and the upper surface of the test strip port 64, which is held in the port shroud 54, are induced to be maintained in a position parallel to both the upper surface of the vacuum plate 60 and the top interior surface 71 of the cover 12a when the cover 12a is in the closed position. The operation of the second resilient biasing element 67 is described below, as it relates to the steps involved in moving the movable support 58. The skirt 56 has an opening 72 formed therein through which the lancet 74 passes during the lancing step of the method of this invention. The lancet 74 is analogous to the lancet 32 shown in FIGS. 1A and 1B. The vacuum plate 60 functions to ensure that a vacuum is maintained in the chamber enclosed by the cover 12a and the skirt 56. The diaphragm 62 functions as the agent that causes the movable support 58 to move sufficiently to move test strip port 64 sufficiently to properly align the test strip with the sealable opening 24 in the cover 12a of the housing 12. The ultimate function of the movable support 58 is to move the test strip port 64 sufficiently to properly align an opening 70a in the test strip 70 with the sealable opening 24 in the cover 12a of the housing 12. In order to perform this function, the movable support 58 also supports the port shroud 54, which contains the test strip port 64.

In the embodiment shown in FIGS. 2B, 3C, 5A–5D, 7A–7C, 8A–8C, 9A–9B, the movable support 58 is an L-shaped structure having a leg 58a and a base 58b. A pivot 75 is included at the junction of the leg 58a and the base 58b. The pivot 75 can be of simple construction, such as, for example, at least one shaft supported in at least one bearing. The movable support 58 is capable of rotation about this pivot 75 at an angle of rotation sufficient to move the test strip port 64 a sufficient lateral distance toward the sealable opening 24 in the cover 12a of the housing 12, whereby an opening 70a in the test strip 70 is placed in register with the sealable opening 24 in the cover 12a of the housing 12. The base 58b is of sufficient length that the end thereof located distally of the pivot 75 can be moved vertically by expansion of the diaphragm 62 when the diaphragm 62 is subjected to a pressure gradient. The force needed to actuate the diaphragm 62 is furnished by the ambient pressure, which is the pressure within the body 12b of the housing 12. The leg 58a must of sufficient length to position the port shroud 54 sufficiently close to the top interior surface 71 of the cover 12a (when the cover 12a is closed), so that when a test strip 70 is inserted in the test strip port 64, the test strip 70 will be sufficiently close to the sealable opening 24 in the cover 12a of the housing 12 so that a sample of blood or other body fluid for an assay can be collected successfully. The movable support 58 is connected to the port shroud 54 by means of a pivot 76. Like the pivot 75, the pivot 76 can be of simple construction, such as, for example, at least one shaft supported in at least one bearing. This type of connection is used so that when (1) the diaphragm 62 expands, (2) the base 58b is raised, and (3) the leg 58a is tilted at a sufficient angle, the pivot 76 will allow the test strip port 64 of the port shroud 54 to move from a first position to a second position, at which second position the end 70b of the test strip 70 located distally from the end 70c of the test strip 70 inserted in the test strip port 64 will abut a test strip stop 76 located on the cover 12a of the housing 12, thereby placing the opening 70a of the test strip 70 in register with the sealable opening 24 in the cover 12a of the housing 12. The second biasing element 67, which was disclosed earlier, operates to urge the leg 58a of the movable support 58 to its upright position when the diaphragm 62 is not being subjected to a pressure gradient.

Referring specifically now to FIGS. 5A, 5B, 5C, and 5D, the test strip port 64 comprises a "no touch" switch 80 and a biasing bar 82. When a test strip 70 is inserted into the test strip port 64, the force of the biasing bar 82 acting upon the upper surface of the test strip 70 causes the "no touch" switch 80 to close. When the "no touch" switch 80 closes, a signal indicates that the lancing phase of the assay can begin.

Referring specifically now to FIGS. 6A, 6B, 6C, and 6D, registration of the test strip 70 in the apparatus in the latitudinal direction is accomplished as the cover 12a of the housing 12 is closed. As the cover 12a of the housing 12 is closed, the latitudinal registration features 84 disposed on the cover 12a interlock with latitudinal registration features 86 disposed on the port shroud 54. This interlocking action precisely positions the test strip 70 in the latitudinal direction.

All of the parts of the alignment mechanism are preferably made of molded plastic, with the exception of the diaphragm 62, which is preferably made of a flexible elastomeric material, and the biasing elements 66 and 67, which are preferably helical springs formed from metal. Of course, the electrical contacts in the test strip port 64 and the electrical contacts of the "no touch" switch 80 are preferably made of electrically conductive metal. The biasing bar 82 is preferably made of metal.

OPERATION

Figure 4:
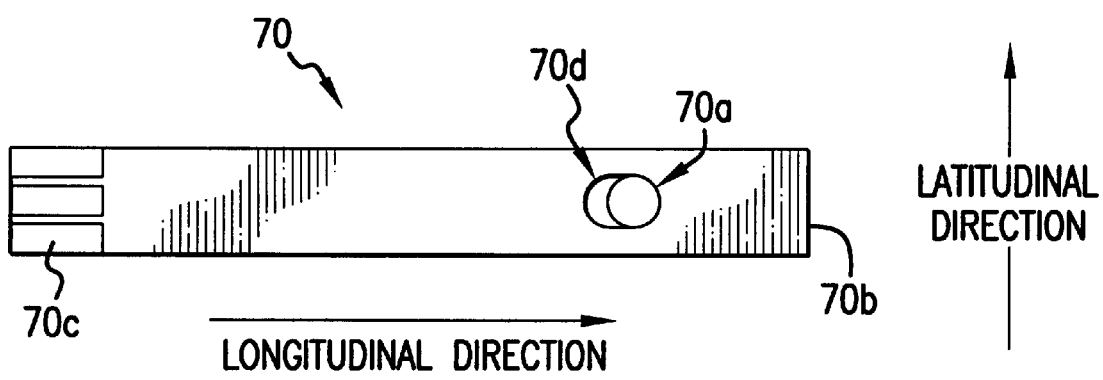
FIG. 4 is a top view of a fluid collector suitable for use in this invention.
Figure 5A:
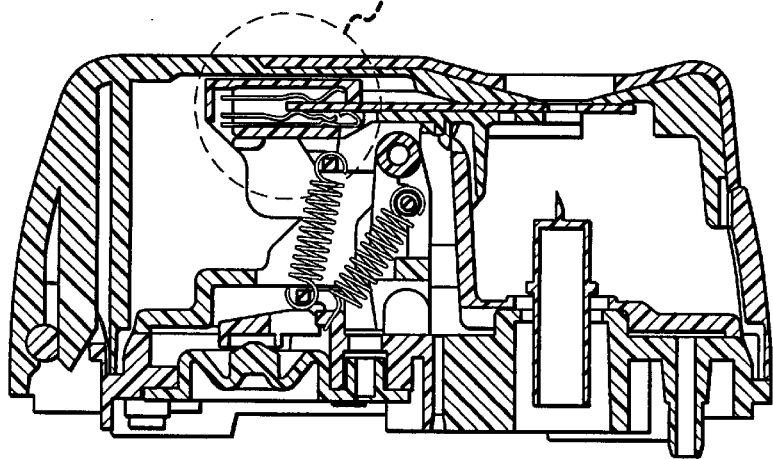
FIG. 5A is the same view as FIG. 3C, but indicating the area to be enlarged in FIGS. 5B, 5C, and 5D.
Figure 5B:
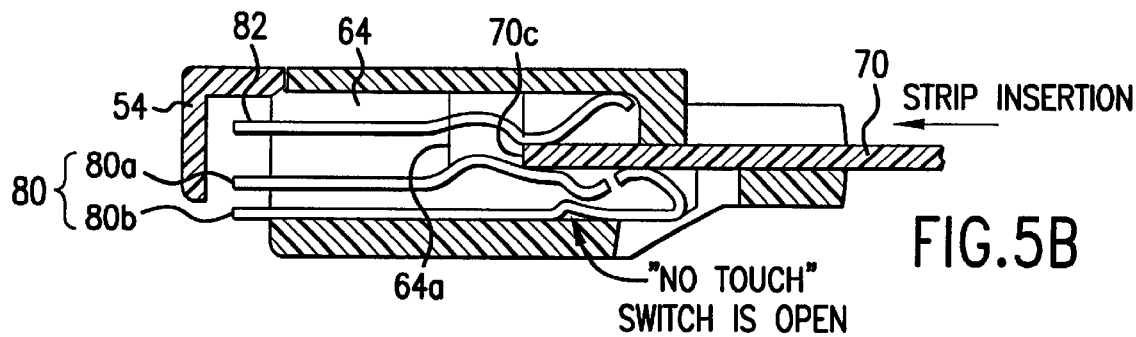
FIGS. 5B, 5C, and 5D are side elevation views, greatly enlarged, in cross section, of the switch that indicates when the fluid collector is in position for an assay.
Figure 5C:
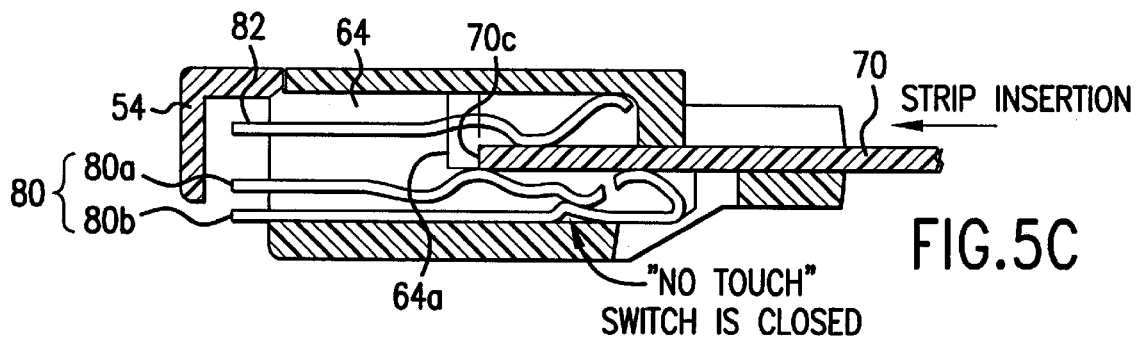
Figure 5D:
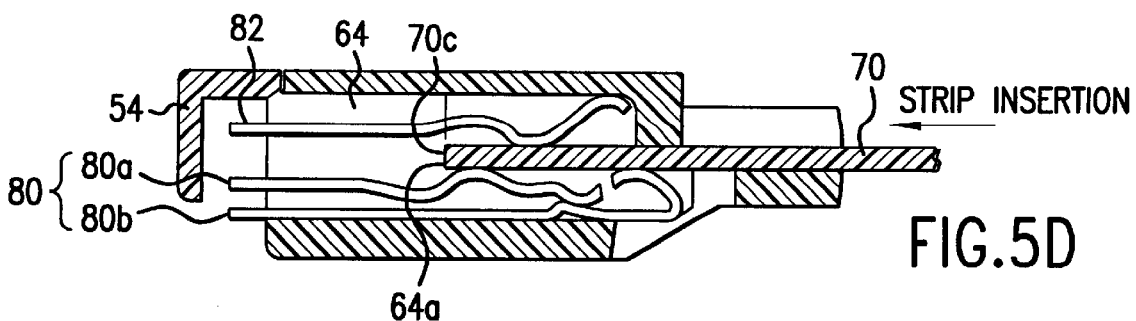
Figure 6A:
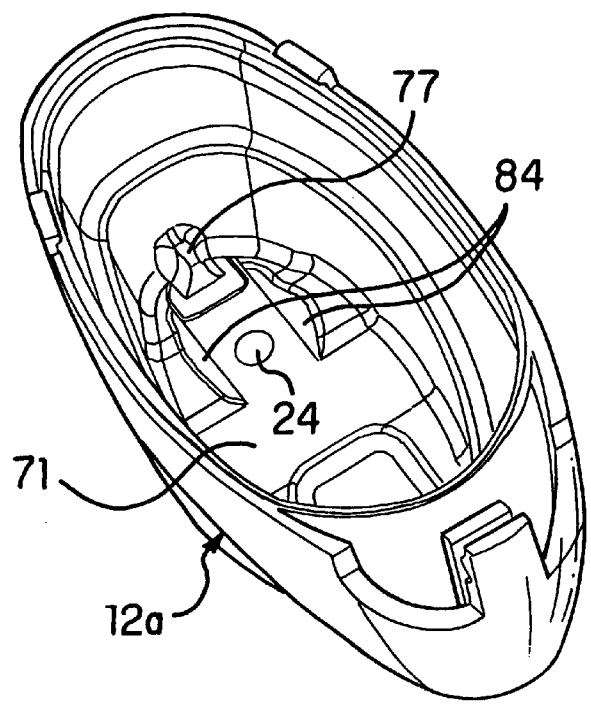
FIG. 6A is a perspective view of the interior of the cover.
Figure 6D:
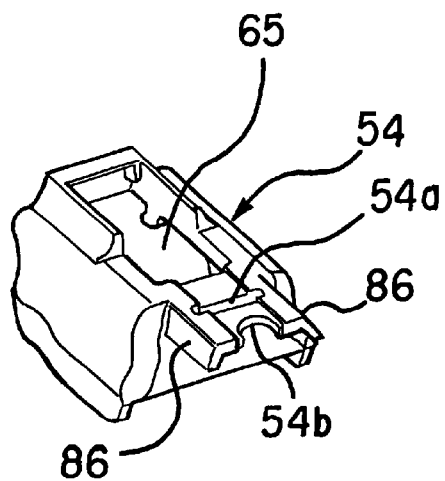
FIG. 6D is a perspective view of the port shroud and the test strip port of the alignment mechanism assembly of this invention.
Figure 6C:
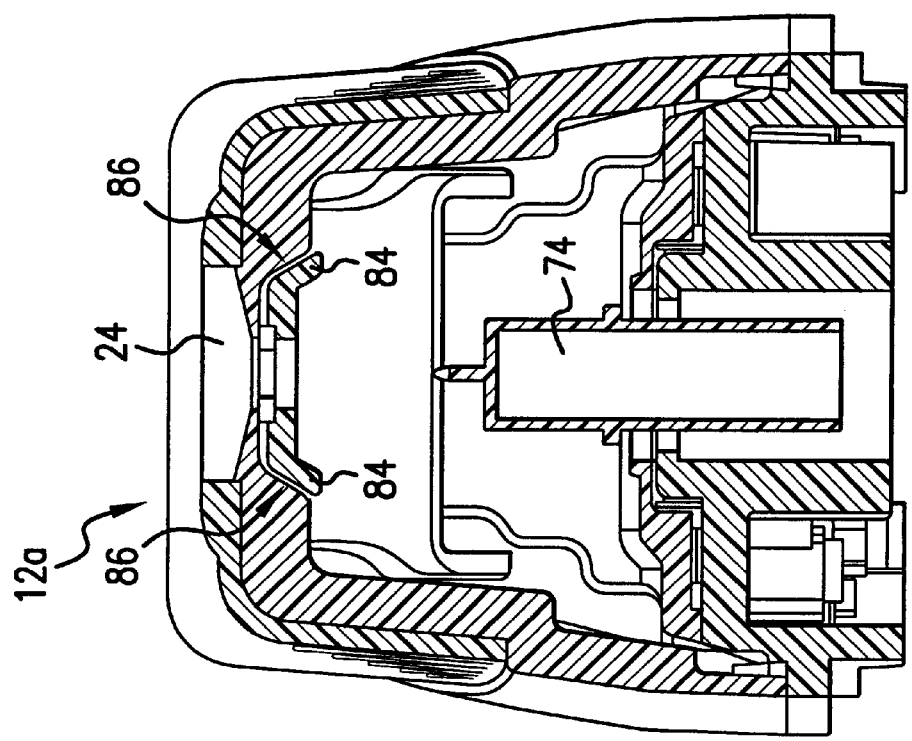
FIG. 6C is a front elevation view, in cross section, taken along line C—C of FIG. 6B, of the cover and the alignment mechanism assembly of this invention.
Figure 6B:
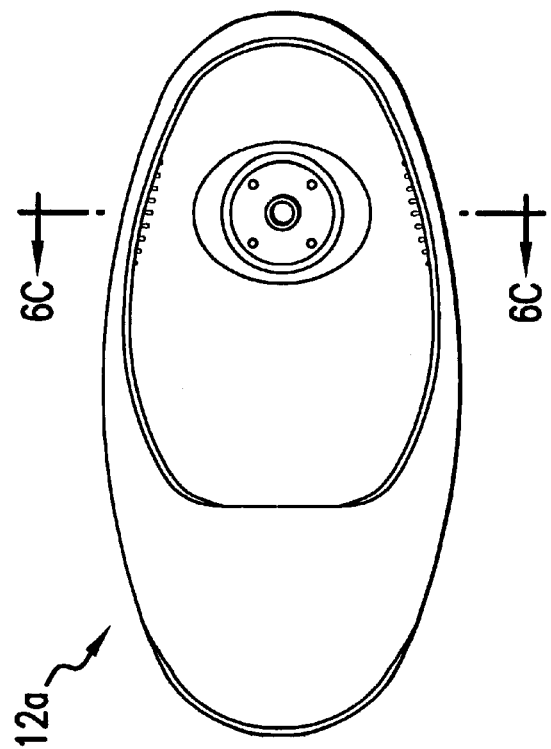
FIG. 6B is the same view as FIG. 3A.
Figure 7A:
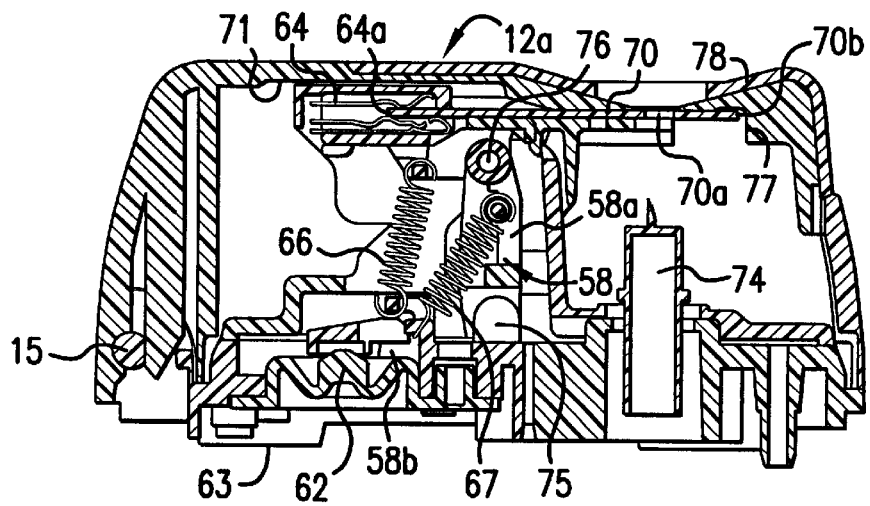
FIGS. 7A, 7B, and 7C are side elevation views, in cross section, of the fluid collector and alignment mechanism assembly showing the sequence for properly aligning the fluid collector for an assay.
Figure 7B:
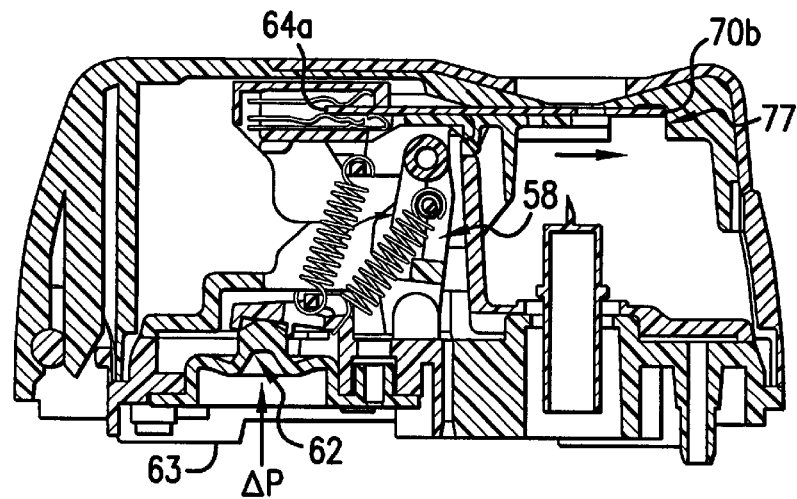
Figure 7C:
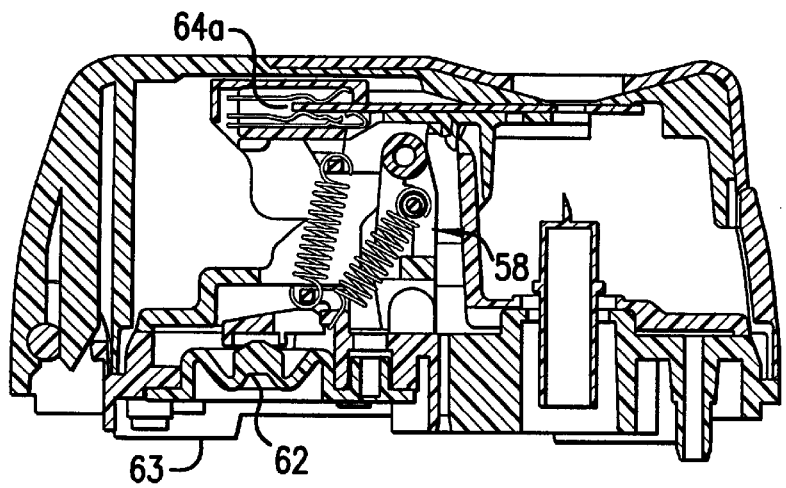
Figure 8A:
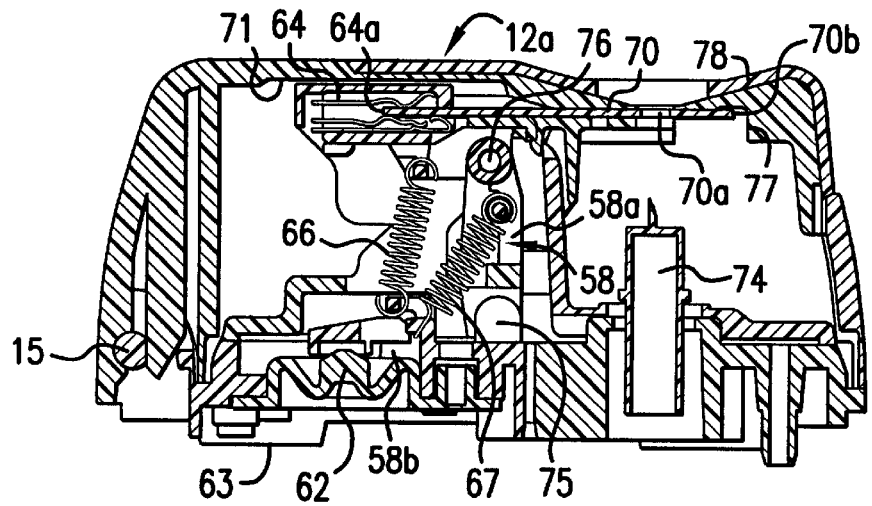
FIGS. 8A, 8B, and 8C are side elevation views, in cross section, of the fluid collector and alignment mechanism assembly showing the sequence for operating the lancing assembly for collecting a sample of blood for an assay.
Figure 8B:
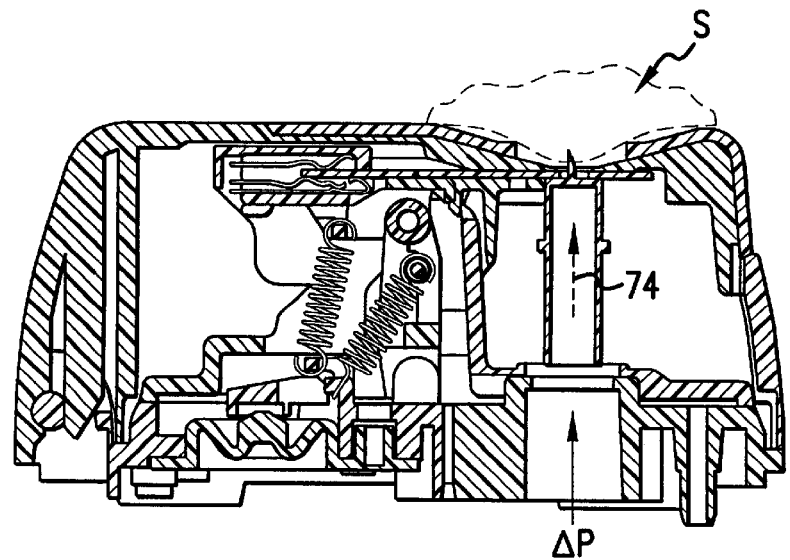
Figure 8C:
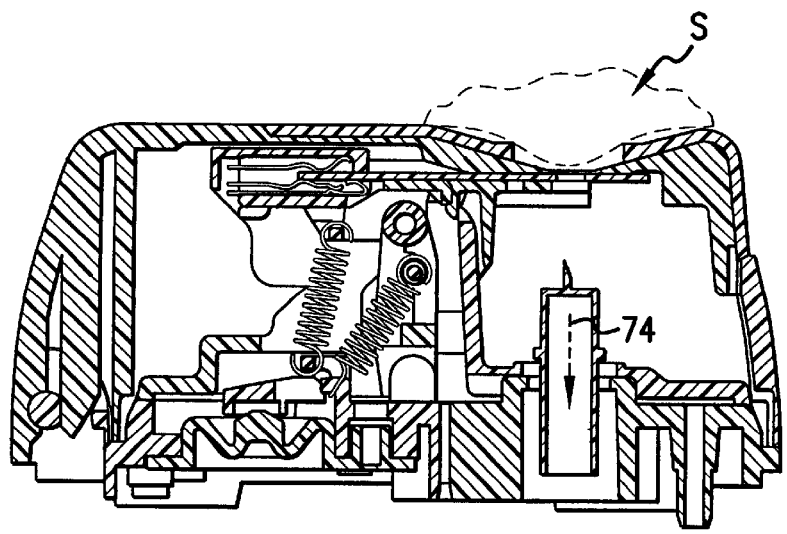
Figure 9A:
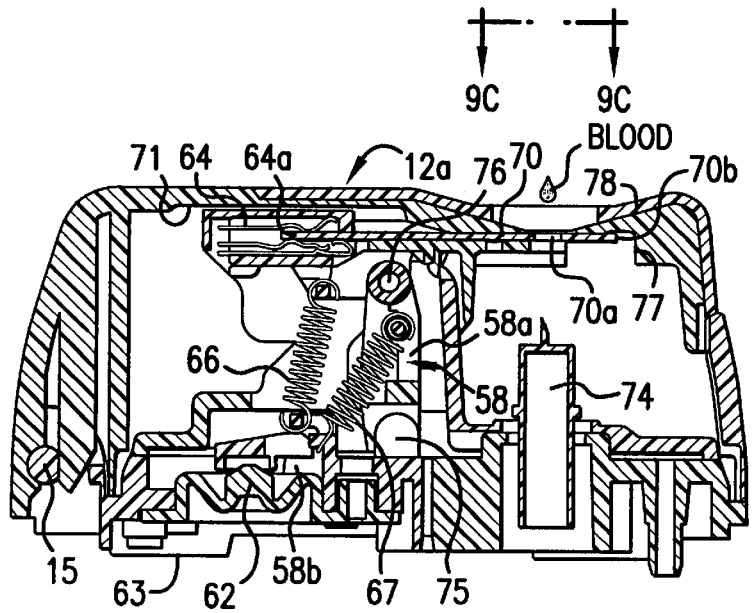
FIGS. 9A and 9B are side elevation views, in cross section, of the sample collection procedure.
Figure 9C:
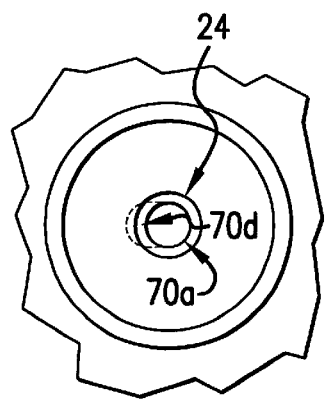
FIG. 9C is a top view of the blood collection area of the apparatus taken along line C—C of FIG. 9A.
Figure 9B:
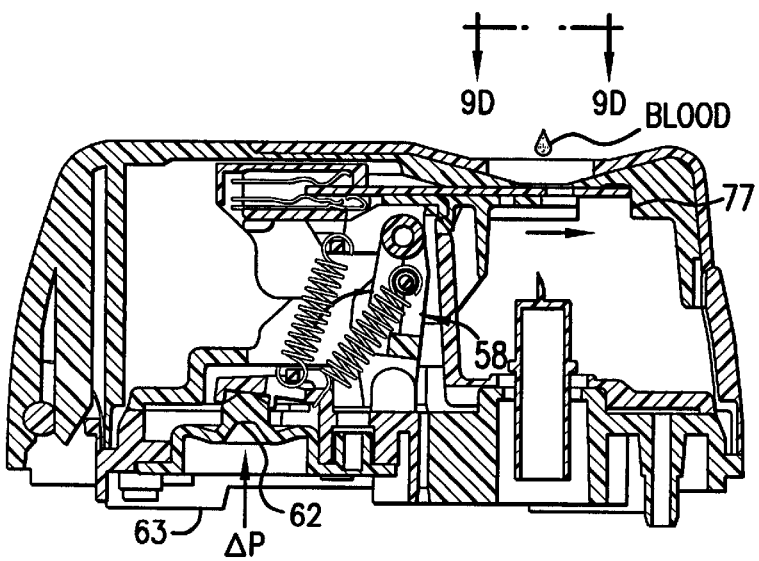
Figure 9D:
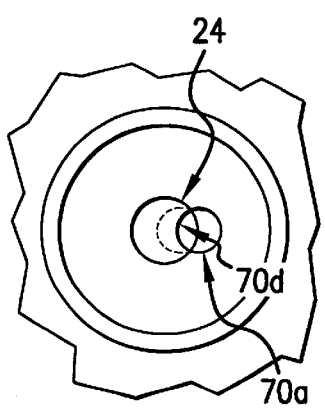
FIG. 9D is a top view of the blood collection area of the apparatus taken along line D—D of FIG. 9B. The components of the alignment mechanism assembly in FIG. 9B are identical to those of the alignment mechanism assembly in FIG. 9A. Therefore, reference numerals that are not relevant to the sample collection procedure are not restated in FIG. 9B.

Operation of the apparatus 10 will now be described. FIG. 4 illustrates a test strip suitable for use in this invention. FIGS. 5A, 5B, 5C, and 5D illustrate the operation of the switch that indicates when a test strip 70 is inserted in the test strip port 64. FIGS. 7A, 7B, and 7C illustrate how the apparatus aligns the opening 70a of the test strip 70 with the sealable opening 24 of the cover 12a of the housing 12 prior to lancing or prior to collecting a sample of blood. FIGS. 8A, 8B, and 8C illustrate the key steps of the lancing procedure. FIGS. 9A, 9B, 9C, and 9D illustrate alignment of the opening 70a of the test strip 70 with the sealable opening 24 of the cover 12a of the housing 12 during the blood collection step.

The test strip 70 is specifically designed to fit in to the test strip port 64. The test strip port 64 includes a "no touch" switch 80. This "no touch" switch 80 indicates when a test strip 70 has been inserted into the test strip port 64. As a test strip 70 is being inserted into the test strip port 64, the test strip 70 deflects the "no touch" contact 80a until the "no touch" contact 80a makes electrical contact with a "pull up" contact 80b, thereby causing the apparatus to be electrically actuated, so that an assay can be performed. Downward force provided by the biasing bar 82 aids the test strip 70 in bringing about contact of the "no touch" contact 80a and the "pull up" contact 80b. See FIGS. 5A, 5B, 5C, and 5D. However, even though the "no touch" contact 80a makes electrical contact with the "pull up" contact 80b, the user cannot be certain that the test strip 70 has been properly positioned in the test strip port 64. For example, the end 70c of the test strip 70 that contacts the "no touch" switch 80 is designed so that it abuts against the end 64a of the test strip port 64. In a worst case situation, this end 70c of the test strip 70 could be a small distance, e.g., 0.045 inch from the end 64a of the test strip port 64. This failure of the end 70c of the test strip 70 to abut the end 64a of the test strip port 64 directly translates to a misalignment between the opening 70a in the test strip 70 and the sealable opening 24 in the cover 12a. If this misalignment is not corrected, the lancet 74, when triggered, could possibly strike a solid portion of the test strip 70 and fail to pass through the opening 70a in the test strip 70, and, consequently (1) fail to pass through the sealable opening 24 in the cover 12a, (2) fail to lance the patient, and (3) fail to allow access to a blood sample. In order to correct for any possibility of misalignment of the test strip 70 in the apparatus, the apparatus undergoes the following procedure.

After the test strip 70 is inserted into the test strip port 64, the cover 12a of the housing 12 is closed against the body 12b of the housing 12. A pressure gradient is applied to the diaphragm 62. The pressure gradient causes the diaphragm 62, which is preferably made of a flexible elastomeric material, to expand. This expansion of the diaphragm 62 causes the base 58b of the movable support 58 to move upwardly, thereby causing the movable support 58 to tilt forward, i.e., toward the sealable opening 24 in the cover 12a, via the pivot 75. As the movable support 58 tilts forward, the pivot 76 allows the test strip port 64 to move forward, i.e., toward the sealable opening 24 in the cover 12a. By this movement, the end 70b of the test strip 70 is caused to abut against a test strip stop 77, which projects from the cover 12a of the housing 12. Because the force supplied by the diaphragm 62 exceeds the static friction force existing between the test strip 70 and the test strip port 64, the test strip 70 is pushed backward into the test strip port 64 until the end 70c of the test strip 70 abuts the end 64a of the test strip port 64. At this point, the test strip 70 is fully seated in the test strip port 64, and, consequently, is properly aligned in the apparatus 10. In other words, the opening 70a in the test strip 70 is properly aligned with the sealable opening 24 in the cover 12a of the housing 12. Then the pressure gradient is removed, the diaphragm 62 deflates, and the movable support 58 is reset. The second biasing element 67 operates to urge the leg 58a of the movable support 58 to its upright position when the diaphragm 62 is not being subjected to a pressure gradient. The apparatus is now ready to commence the lancing phase of the assay. See FIGS. 7A, 7B, and 7C.

In order for the diaphragm 62 to be actuated to initiate the operation of the alignment mechanism assembly 50, the pressure to which the diaphragm 62 is subjected must be varied at the appropriate times to bring about the pressure gradient previously mentioned. Referring now to FIGS. 7A through 9D, inclusive, during the time the vacuum pump (not shown) of the apparatus 10 is in operation, the pressure within the volume enclosed by the vacuum plate 60 and the cover 12a of the housing 12 is below the ambient pressure. It should be mentioned at this point that in order to maintain the pressure within the volume enclosed by the vacuum plate 60 and the cover 12a of the housing 12 below the ambient pressure while the vacuum pump is in operation, the sealable opening 24 in the cover 12a of the housing 12 must be sealed. The seal is formed by a seal 78 placed against the surface of the skin, designated herein by the letter "S". Additional details relating to the seal 78 will be described below. In order to simplify the explanation of the steps involved in varying the pressure for operating the diaphragm 62, it will be assumed that when the vacuum pump is operating, the pressure within the volume enclosed by the vacuum plate 60 and the cover 12a of the housing 12 is 6.7 psi, while the ambient pressure is 14.7 psi. The pressure within the body 12b of the housing 12 is the ambient pressure. These particular values of pressure are not required, but in all cases the pressure within the body 12b of the housing 12 exceeds the pressure within the volume enclosed by the vacuum plate 60 and the cover 12a of the housing 12 when the vacuum pump is operating. As the vacuum pump is operating, the diaphragm 62 is maintained in an equilibrium condition, wherein the pressure upon the diaphragm 62 is below ambient pressure. For example, the pressure of the equilibrium condition is 6.7 psi. The diaphragm 62 is maintained in this equilibrium condition by means of the diaphragm plate 63, which separates the diaphragm 62 from the body 12b of the housing 12. In other words, when the vacuum pump is operating, both the surface of the diaphragm 62 facing the cover 12a of the housing 12 is under a pressure (e.g., 6.7 psi) below ambient pressure (e.g., 14.7 psi) and the surface of the diaphragm facing the body 12b of the housing 12 is under a pressure (e.g., 6.7 psi) below ambient pressure (e.g., 14.7 psi). The diaphragm 62 is connected to the ambient environment of the body 12b of the housing 12 by means of a passageway (not shown), which faces the surface of the diaphragm 62 facing the body 12b of the housing 12. In the passageway is a valve (not shown), such as, for example, a solenoid valve. The passageway is blocked when the valve is closed; the passageway is open when the valve is open. When the valve is closed, the pressure on the diaphragm 62 is the equilibrium condition pressure, e.g., 6.7 psi, which is below ambient pressure (e.g., 14.7 psi). When it is the appropriate time for the test strip 70 to be properly aligned, a signal provided by the electronics causes the valve to be opened, thereby allowing ambient air to impinge upon the surface of the diaphragm 62 facing the body 12b of the housing 12. This influx of ambient air increases the air pressure impinging upon the diaphragm 62, thereby causing the diaphragm 62 to expand. The expansion of the diaphragm 62 causes the base 58b of the support 58 to be raised, thereby causing the leg 58a of the support 58 to be tilted toward the opening 24 in the cover 12a of the housing 12. When it is time for the support 58 to be reset, a signal from the electronics causes the valve to be closed, thereby allowing the pressure upon the diaphragm 62 to reach its equilibrium condition, e.g., 6.7 psi. At that pressure, the diaphragm 62 remains in its normal, unexpanded position.

After the test strip 70 has been correctly positioned and aligned in the apparatus 10, the lancing assembly can form an opening in the skin of the patient. As indicated previously, the seal 78 of the apparatus 10 has been placed against the surface of the skin, designated herein by the letter "S", to maintain the pressure within the volume enclosed by the vacuum plate 60 and the cover 12a of the housing 12 below the ambient pressure while the vacuum pump is in operation. The seal 78 is analogous to the seal 20 shown in FIGS. 1A and 1B. The purpose of the seal 78 is to prevent air from leaking into apparatus 10, so that the vacuum pump (not shown in FIGS. 1A and 1B) can provide sufficient suction action for (1) increasing the availability of blood to the area of the skin from which the sample is to be collected, (2) stretching the skin, and (3) collecting the sample of blood from an unobstructed opening in the skin. The seal 78 surrounds the sealable opening 24 in the cover 12a of the housing 12. The sealable opening 24 in the cover 12a allows communication between the surface of the skin and the test strip 70. The seal 78 is preferably made of a rubber or an elastomeric material. After an appropriate period of time, a pressure gradient is applied to the lancing assembly, thereby triggering the lancet 74, which is propelled toward the sealable opening 24 in the cover 12a at a nominal rate of speed, for example, 3.3 m/sec. The lancet 74 passes through the opening 70a in the test strip 70, the sealable opening 24 in the cover 12a, and contacts the skin of the patient at a sufficient rate of speed to form an opening in the skin of the patient. Then the pressure gradient is removed and the lancing assembly retracts the lancet 74 to its original unfired position. Alternatively, if the test strip 70 is of the type that has a semi-circular notch at the end 70b thereof, the lancet 74 passes the end 70b of the test strip 70. See FIGS. 8A, 8B, and 8C.

After an opening has been formed in the skin of the patient, the sample, for example, a blood sample, can be collected so that an assay can be performed. The sample collection sequence is as follows. First, a pressure gradient is applied to the diaphragm 62. The pressure gradient causes the diaphragm 62 to expand. This expansion of the diaphragm 62 causes the base 58b of the movable support 58 to move upwardly, thereby causing the movable support 58 to tilt forward, i.e., toward the sealable opening 24 in the cover 12a, via the pivot 75. As the movable support 58 tilts forward, the pivot 76 allows the test strip port 64 to move forward, i.e., toward the sealable opening 24 in the cover 12a. By this movement, the end 70b of the test strip 70 is caused to abut against a test strip stop 77, which projects from the cover 12a of the housing 12. The test strip stop is designed to allow the alignment mechanism assembly to move the test strip 70 forward a small distance, which distance is equal to the distance between the center of the sealable opening 24 in the cover 12a and the sample collection area 70d located on the test strip 70. As an example, this distance is approximately 0.085 inch. The sample, e.g., blood, emerging from the opening in the skin, begins to contact the sample collection area 70d of the test strip 70. Once the apparatus 10 determines that a sufficient volume of sample has been collected, by means of the electronics, the pressure gradient is removed, by means of a signal from the electronics, the diaphragm 62 deflates, and the movable support 58 is reset. The second biasing element 67 operates to urge the leg 58a of the movable support 58 to its upright position when the diaphragm 62 is not being subjected to a pressure gradient. See FIGS. 9A, 9B, 9C, and 9D. The diaphragm 62 is actuated by means of the procedure relating to alignment of the test strip for the lancing step described previously. The apparatus is now ready to commence the analytical or measurement phase of the assay.

When a sufficient amount of blood has been collected, the test strip 70 then generates a signal, which results in deactivation of the vacuum pump, and the vacuum is released by, for example, an electronically controlled valve. Alternatively, the vacuum pump may be stopped after a pre-set time interval. The apparatus 10 may then be removed from the individual's skin. The apparatus 10 performs the assay and the results are displayed on a display such as for example a liquid crystal display. More particularly, the test strip 70 generates a signal, as described above, indicative of a condition, e.g., blood glucose level, which signal is transmitted via electrical circuitry to the electronics housed in the apparatus 10. The signal is processed by such electronics, in a manner known to those skilled in the art, and the results obtained from the test strip 70 can be displayed on a screen 40, typically a conventional liquid crystal digital display. Other manners of display may also be used.

Upon completion of the measurement, the cover 12a may be opened and the test strip 70 and the lancet 74 may be replaced. The lancet 74 and the test strip 70 may be replaced immediately after use, immediately before use, or may be replaced at any other time.

In the embodiment described herein, the test strip 70 was moved to effect proper alignment by means of an alignment mechanism assembly 50 comprising a port shroud 54, a skirt 56, a movable support 58, a vacuum plate 60, a diaphragm 62, a test strip port 64, and other accessories needed to allow the foregoing components to operate in the manner desired. Alternatively, the test strip 70 may be moved incrementally through the action of a solenoid or other electromechanical device. For example, the test strip 70 may be moved by a movable support that is moved by via a four-bar linkage.

In FIGS. 1A and 1B, an extension 42 extending laterally across the width of the apparatus 10 is shown. When present, the extension 42 stops the lancet assembly from extending beyond the extension 42 and prevents the lancet 74 from extending more than is desired into the skin. The preferred lancing depth typically ranges from about 0.5 mm to about 3 mm into the skin.

Useful practices for various steps related to the overall method, but not specifically related to the method of alignment, will now be described in detail.

An unobstructed opening in the area of the skin from which the sample of blood is to be collected is formed by a piercing device or some other type of device capable of forming an unobstructed opening in the skin. Piercing devices suitable for this invention include, but are not limited to, mechanical lancing assemblies. Other types of devices capable of forming an unobstructed opening in the skin include, but are not limited to, lasers and fluid jets. Other types of devices capable of forming an unobstructed opening in the skin can be used, and this disclosure should not be construed so as to be limited to the devices listed. Mechanical lancing assemblies are well-known in the art. These assemblies comprise standard steel lancets, serrated devices, and multiple tip devices. The lancets can be made from metal or plastic. Multiple tip devices provide redundancy, which can reduce the number of failures and increase the volume of blood collected.

Lasers suitable for forming an unobstructed opening in the skin to draw blood are also well-known in the art. See for example, U.S. Pat. Nos. 4,775,361, 5,165,418, 5,374,556, International Publication Number WO 94/09713, and Lane et al. (1984) IBM Research Report—"Ultraviolet-Laser Ablation of Skin", all of which are incorporated herein by reference. Lasers that are suitable for forming an unobstructed opening in the skin include Er:YAG, Nd:YAG, and semiconductor lasers.

Fluid jets suitable for forming an unobstructed opening in the skin employ a high pressure jet of fluid, preferably a saline solution, to penetrate the skin.

Regardless of what type of device is utilized to form an unobstructed opening in the skin, the opening formed by the device must be unobstructed. As used herein, the term "unobstructed" means free from clogging, hampering, blocking, or closing up by an obstacle. More specifically, the expressions "unobstructed opening in the area of the skin from which the sample is to be collected", "unobstructed opening in the skin", and the like are intended to mean that the portion of the opening below the surface of the skin is free from any foreign object that would clog, hamper, block, or close up the opening, such as, for example, a needle of any type. For example, if a lancet is used to form the opening, it must be retracted from the opening prior to the commencement of the collection of blood. Because lasers and fluid jets do not require contact with the skin to form openings in the skin, these types of devices typically provide unobstructed openings. However, these expressions are not intended to include foreign objects at the surface of the skin or above the surface of the skin, such as, for example, a glucose monitor. By leaving the opening unobstructed, blood can be collected much more rapidly from the opening than it would be collected if the piercing and cutting means were allowed to remain in the opening. In addition, the requirement of an unobstructed opening exposes the body to a foreign object either not at all or for only a very short period of time, which is welcomed by the patient.

The step of collecting the sample of blood from the opening in the skin is carried out by a combination of collection enhancing elements. Collection enhancing elements suitable for use in this invention include, but are not limited to, vacuum, skin stretching elements, and heating elements. When these elements are used in combination, the volume of blood collected is greatly increased, particularly when a vacuum is applied in combination with skin stretching. In this combination, the vacuum not only causes the blood to be rapidly removed from the unobstructed opening by suction, it also causes a portion of the skin in the vicinity of the opening to be stretched. Stretching of the skin can be effected by other means, such as mechanical means or adhesives. Mechanical means include devices for pinching or pulling the skin; adhesives bring about stretching of the skin by means of pulling. It is preferred to use a vacuum to effect stretching of the skin. Like a vacuum, a heating element operates more effectively in combination with other techniques, e.g., stretching of the skin.

In the preferred embodiment of this invention, step (d), the step of forming the unobstructed opening, is preceded by the step of increasing the availability of blood at the area of the skin from which the sample is to be collected. The availability of blood at a given area of the skin can be increased by at least two methods. In one method, a vacuum can be used to cause blood flowing through blood vessels to pool in the area of the skin where the vacuum is applied. In another method, heat can be used to cause blood flowing through blood vessels to flow more rapidly in the area of the skin where heat is applied, thereby allowing a greater quantity of blood to be collected from the blood collection site per unit of time. Although the step of increasing the availability of blood in the vicinity of the blood collection site is not required, the employment of this step can result in a greater volume of blood collected. Elements for increasing the availability of blood at a blood collection site that are suitable for use in this invention include, but are not limited to, vacuum, localized heating element, skin stretching element, and chemicals. As stated previously, applying a vacuum to the area of the skin from which blood is to be collected can increase blood availability under and within the skin at the application site. The vacuum can also be used to stretch the skin upwardly into a chamber, thereby increasing pooling of blood under and within the skin. This combination of vacuum and skin stretching can be an extension of the combination used to collect blood from the opening in the skin, as previously described. It is well-known that heat can increase perfusion on the large scale of a limb or a finger. Chemical means, such as histamine, can be used to cause a physiological response to increase perfusion under and within the skin.

Specifications for various components related to the overall apparatus 10, but not specifically related to the alignment will now be described in detail. Referring again to FIGS. 1A and 1B, the apparatus 10 comprises a housing 12, and disposed within the housing 12 are a vacuum pump (not shown), a lancing assembly (not shown), a battery (not shown), and electronics (not shown). A switch 22 is provided to activate electronics.

The housing 12 is preferably made from a plastic material. It is preferably of sufficient size to contain all of the components that are required for forming an unobstructed opening in the area of the skin from which the sample of blood is to be collected, collecting the sample of blood from the unobstructed opening in the skin, preferably with the aid of a vacuum and a stretching of the skin, and collecting the collected sample in an amount sufficient to carry out a diagnostic test. Methods of preparing the housing 12 are well-known to one of ordinary skill in the art.

The vacuum pump must be capable of providing a vacuum that will provide sufficient suction to stretch the portion of the skin in the region from which the sample of blood is to be collected. Typically, the portion of stretched skin is raised a distance of 1 to 10 mm, preferably 3 to 5 mm, from the plane of the body part of which it is a portion. As the suction provided by the vacuum pump is stretching the appropriate portion of skin, the suction provided by the vacuum pump also causes the stretched portion to become engorged with blood. The level of suction provided must be sufficient to cause a relatively large volume of blood to become engorged at the point that the vacuum is applied. The vacuum pump must also be capable of providing sufficient suction to collect blood from the opening in the skin at a rate sufficient to collect at least 1 $\mu$L of blood within a period of five minutes. A vacuum pump that is suitable for the device of this invention can be a diaphragm pump, a piston pump, a rotary vane pump, or any other pump that will perform the required functions set forth previously. Typically, the vacuum pump employs a self-contained permanent magnet DC motor. Vacuum pumps that are suitable for this invention are well-known to those of ordinary skill in the art and are commercially available. A vacuum pump suitable for use in the present invention is available from T-Squared Manufacturing Company, Nutley, N.J., and has the part number T2-03.08.004.

The vacuum pump is preferably capable of providing a pressure of down to about −14.7 psig (0 psi), and is more preferably operated at from about −3.0 psig (11.7 psi) to about −10.0 psig (4.7 psi). The area of the skin subjected to vacuum preferably ranges up to about 50 cm$^2$, more preferably from about 0.1 to about 5.0 cm$^2$. The period of vacuum application prior to forming the opening in the skin, i.e., for increasing the availability of blood to the application site, preferably ranges up to about 5 minutes, preferably from about 1 to about 15 seconds. The period of vacuum application subsequent to forming the opening in the skin, i.e., for aiding in the collection of blood from the unobstructed opening, preferably ranges up to about 5 minutes, preferably from about 1 to about 60 seconds. The vacuum provided by the vacuum pump can be continuous or pulsed. A continuous vacuum is preferred for the reason that it requires fewer components than does a pulsed vacuum. It is preferred that the vacuum applied not cause irreversible damage to the skin. It is preferred that the vacuum applied not produce bruises and discolorations of the skin that persist for several days. It is also preferred that the level of vacuum applied and duration of application of vacuum not be so excessive that it causes the dermis to separate from the epidermis, which results in the formation of a blister filled with fluid.

The lancing assembly comprises at least one lancet. Standard lancets can be used in the lancing assembly of this invention. Narrow gauge (28 to 30 gauge) lancets are preferred. Lancets suitable for this invention can be made from metal or plastic. Lancets suitable for this invention can have single points or multiple points. The depth of penetration of the lancet preferably ranges from about 0.4 to about 2.5 mm, more preferably from about 0.4 to about 1.6 mm.

The length of the lancet or lancets preferably ranges from about 1 mm to about 5 mm. The lancing assembly is preferably located so that the user can easily replace used lancets. The lancet of the lancing assembly can be cocked manually or automatically, e.g., by means of a vacuum-actuated piston or diaphragm. The lancet of the lancing assembly can be triggered manually or automatically, e.g., by means of a vacuum-actuated piston or diaphragm.

Lancing assemblies are well-known in the art. Representative examples of lancing assemblies suitable for this invention are described in U.S. Pat. Nos. Re. 32,922, 4,203,446, 4,990,154, and 5,487,748, all of which are incorporated herein by reference. A particularly suitable lancing assembly for this invention is described in U.S. Pat. No. Re. 32,922. However, any lancing assembly selected should operate in conjunction with the other features of the apparatus 10 of this invention. For example, if a vacuum is employed, the lancing assembly must be designed so that a vacuum can be formed and drawn through the assembly. The lancing assembly can be designed to allow automatic cocking and automatic triggering of the lancet.

While conventional lancing assemblies are suitable for use in this invention, a lancing assembly that utilizes differential gas pressure to thrust a lancet into skin tissue has been developed for use with this invention.

A source of power for the vacuum pump can be disposed within the housing 12. A source of power suitable for the device of this invention is a battery. Alternatively, an external source of power can be used to operate the vacuum pump. The power source is actuated by the electronics, which, in turn, is actuated by the switch 22.

The electronics may incorporate a microprocessor or microcontroller. The function of the electronics is to switch power on and off to operate the various components in the apparatus 10. These components include, but are not limited to, the vacuum pump. The electronics can also be use to switch power on and off to operate components in alternative embodiments, e.g., heating elements, lancets, indicating devices, and valves. Electronics suitable for this invention is the "TATTLETALE MODEL 5F" controller/data logger, commercially available from Onset Computer Corporation, 536 MacArthur Blvd. P. O. Box 3450, Pocasset, Mass. 02559-3450. Auxiliary electronic devices, such as power transistors, pressure monitors, and OP-Amps (operational amplifiers), may also be required in order to provide an interface between the controller and the operational components. All electronics required for this invention are well-known to one of ordinary skill in the art and are commercially available.

Figure 10:
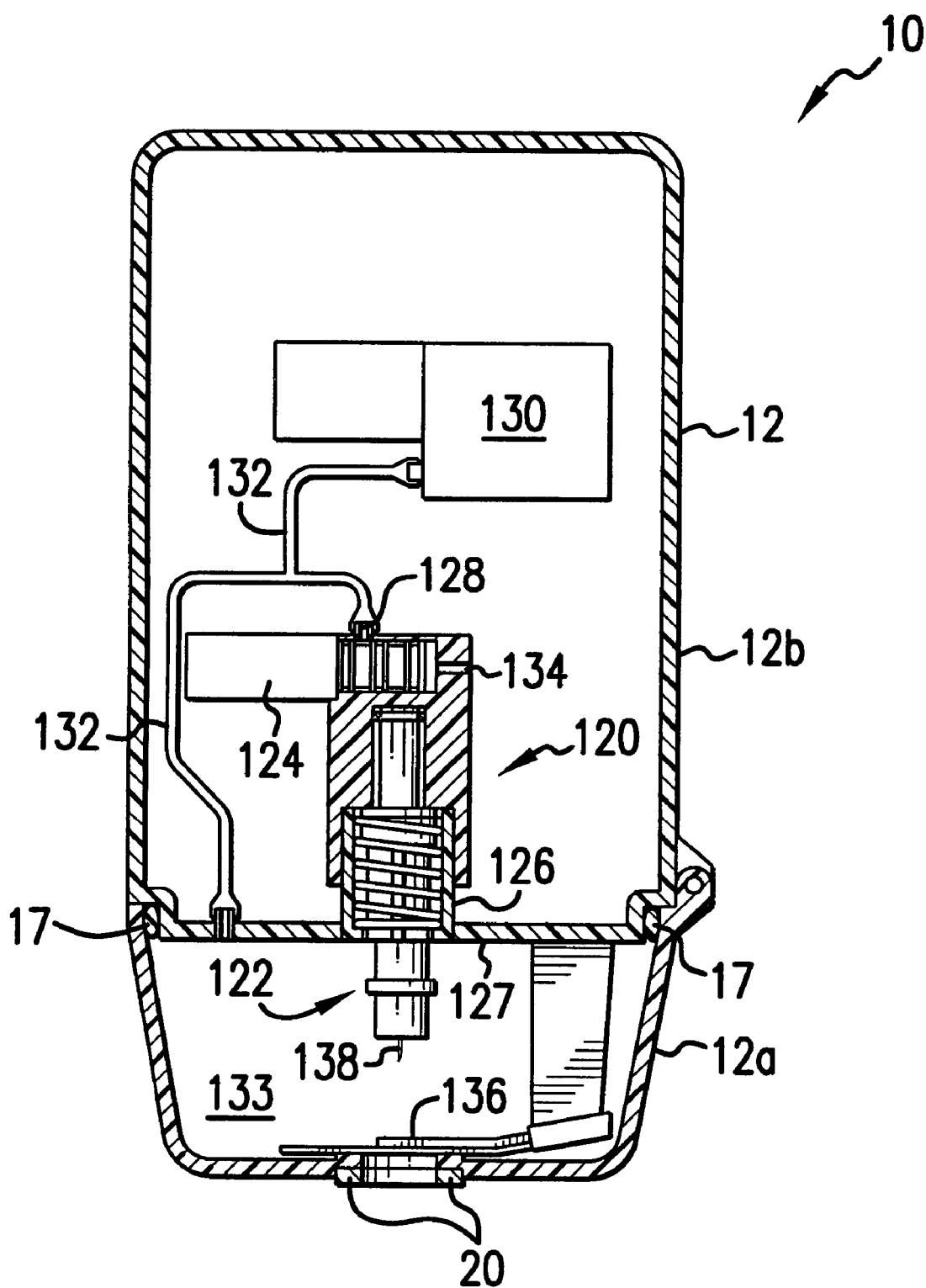
FIG. 10 is a side elevation view, in cross section, of a lancing assembly installed in an embodiment of an apparatus suitable for use in this invention. This figure does not show how the diaphragm of the alignment mechanism assembly is connected to the pump.

FIG. 10 illustrates a preferred installation of the lancing assembly analogous to that shown in FIG. 25 of U.S. Ser. No. 08/982,721, filed Dec. 2, 1997, inside a prototype of an embodiment of the apparatus 10 of this invention. The lancing assembly 120, shown in its retracted pre-thrust position, has been fitted with a standard lancet assembly 122 and a three-way solenoid valve 124. The cap 126 of the lancing assembly 120 is fitted into the partition 127 of the apparatus 10, thereby forming an effective seal against the partition 127. The apparatus 10 comprises a housing 12, which comprises a cover 12a and a body 12b. The exit port 128 of the lancing assembly 120 is connected to a vacuum pump 130 by means of a passageway 132, such as, for example, a connecting tube. The passageway 132 is also connected to a cavity 133 inside the cover 12a of the apparatus 10. In this manner, the vacuum pump 130 can deliver an equal level of vacuum pressure to the cavity 133 and to the exit port 128. The vacuum pressure inside the cavity 133 can be maintained at a level at which the apparatus 10 operates, because the vacuum pump 130 can draw evacuated air from the cavity 133 at a rate faster than the rate at which ambient air leaks into the cavity 133 by way of the door seal 17, the seal placed against the skin of a patient 20, and the seal formed between the cap 126 and the partition 127. The body 12b of the housing 12 of the apparatus 10 contains air having a pressure level equal to the ambient pressure surrounding the apparatus 10. The level of pressure inside the body 12b of the housing 12 does not change during operation of the apparatus 10 because the body 12b of the housing 12 contains a sufficient number of openings (not shown) that communicate with the surrounding ambient air. The air inside the body 12b of the housing 12 can enter the lancing assembly 120 through the inlet port 134 when the solenoid valve 124 is activated to begin the lancing step. The difference in air pressure between the ambient air inside the body 12b of the housing 12 and the evacuated air inside the cavity 133 in the cover 12a of the housing 12 brings about the differential gas pressure needed to operate the lancing assembly. During the lancing step, the thrusting motion of the lancet assembly 122 is halted by a lancet stop 136. The lancet stop 136 has an opening (not shown) that allows the lancet 138 to pass through and penetrate the skin which is placed against the seal 20.

It should be noted that the designs of the various housings shown in FIGS. 1A–10 can be modified without substantially affecting the functioning of the components disposed within the housing or on the surface of the housing. For example, the shapes of the housings, the shapes of the covers of the housings, the shapes of the cover portions of the housings, and the shapes of the remaining portions of the housings can be modified without departing from the scope and spirit of this invention.

This invention provides numerous advantages over blood collection devices of the prior art. Among these advantages are the following:

1. Ability to use parts of the body, other than the finger, as a site for the collection of blood;
2. Reduction of pain by eliminating the need to lance the finger;
3. Increase in speed of collection of blood samples by means of pretreatment comprising a combination of stretching of the skin in conjunction with heat or vacuum or both heat and vacuum;
4. Incorporation of glucose detector in apparatus for collecting the blood sample;
5. Ability to minimize user errors, which typically arise upon insertion of the test strip;
6. Ability to provide automatic transfer of samples;
7. Ability to provide reproducible transfer of samples;
8. Ability to properly align the glucose detector in the apparatus so that the lancet does not strike the glucose detector during the lancing step and the blood emerging from the lanced skin contacts the appropriate location of the glucose detector.

Various modifications and alterations of this invention will become apparent to those skilled in the art without departing from the scope and spirit of this invention, and it should be understood that this invention is not to be unduly limited to the illustrative embodiments set forth herein.

What is claimed is:

1. An apparatus suitable for obtaining a sample of blood for analysis in a diagnostic test, comprising:

(a) a housing having a sealable chamber located therein and a sealable opening in fluid communication with said sealable chamber;
    (b) a vacuum pump in communication with said sealable chamber;
    (c) a device for forming an unobstructed opening in an area of skin from which a sample is to be collected, said device positioned within said sealable chamber;
    (d) a movable support for supporting and positioning a port for a fluid collector in said sealable chamber, said movable support capable of moving said port within said sealable chamber between a first position and a second position; and
    (e) a stop for aligning said fluid collector.

2. The apparatus of claim 1, wherein said housing comprises:

(a) a body, and
    (b) a cover, said cover positionable over said body and including said sealable opening.

3. The apparatus of claim 1, wherein said fluid collector is a test strip.

4. The apparatus of claim 3, wherein said test strip has an opening therein.

5. The apparatus of claim 1, wherein said stop (e) projects from said cover of said housing.

6. The apparatus of claim 1, wherein said movable support (d) supports a test strip port.

7. The apparatus of claim 6, wherein said test strip port is enclosed by a port shroud.

8. The apparatus of claim 6, wherein said test strip port includes a switch.

9. The apparatus of claim 8, wherein said switch comprises a "no touch" contact and a "pull up" contact.

10. The apparatus of claim 1, further including a means for preventing said sample from reaching and contaminating said port for said fluid collector.

11. The apparatus of claim 1, wherein said port for said fluid collector includes at least one electrical connection.

12. The apparatus of claim 1, wherein said housing contains at least one latitudinal registration feature to position said fluid collector latitudinally.

13. The apparatus of claim 1, wherein said fluid collector comprises a biosensor.

14. The apparatus of claim 13, wherein said biosensor comprises a glucose detector.

15. The apparatus of claim 1, wherein said fluid collector comprises a reflectance strip.

16. The apparatus of claim 15, wherein said reflectance strip comprises a glucose detector.

17. The apparatus of claim 1, further comprising a reflectometer.

18. The apparatus of claim 1, further comprising electronics.

19. The apparatus of claim 18, wherein the electronics control power to said vacuum pump.

20. The apparatus of claim 18, wherein the electronics control power to the lancing assembly.

21. The apparatus of claim 1, wherein movement of said movable support is effected by a diaphragm.

22. The apparatus of claim 21 wherein said diaphragm is capable of being expanded by a pressure gradient.

23. The apparatus of claim 1, further including a power source.

24. The apparatus of claim 23, wherein said vacuum pump is operably connected to said power source.

25. The apparatus of claim 23, further comprising a display operably connected to said power source and said fluid collector.

26. The apparatus of claim 23, further comprising a switch operably connected to said vacuum pump and said lancing assembly through said power source.

27. A method for obtaining a sample of blood for a diagnostic test, said method comprising the steps of:
   (a) providing the apparatus of claim 1;
   (b) inserting a fluid collector into said support;
   (c) aligning said fluid collector latitudinally;
   (d) aligning said fluid collector longitudinally;
   (e) forming an unobstructed opening in the area of the skin from which said sample of blood is to be collected; and
   (f) collecting said sample of blood from said unobstructed opening in said skin, with the aid of vacuum and stretching of the skin.

28. The method of claim 27, further comprising the step of generating a signal indicative of glucose level.

29. The method of claim 27, further including the step of aligning said fluid collector longitudinally after step (e) and before step (f).

30. The method of claim 29, wherein said movement of said fluid collector is effected by a pressure gradient operating upon said movable support.

31. The method of claim 27, wherein steps (c) through (f) include the steps of:
   (i) placing said apparatus over a region on the surface of the skin from which said sample is to be obtained;
   (ii) forming a seal between said apparatus and said surface of the skin;
   (iii) creating a vacuum sufficient to result in said surface of the skin becoming stretched and engorged with blood;
   (iv) triggering a lancing assembly and causing a lancet to penetrate said skin;
   (v) retracting said lancet;
   (vi) withdrawing blood toward and onto a fluid collector; and
   (vii) releasing said vacuum.

* * * * *